(12) United States Patent
Guerrero-Preston et al.

(10) Patent No.: US 8,859,468 B2
(45) Date of Patent: Oct. 14, 2014

(54) HYPERMETHYLATION BIOMARKERS FOR DETECTION OF CERVICAL CANCER

(75) Inventors: Rafael Enrique Guerrero-Preston, Baltimore, MD (US); David Sidransky, Baltimore, MD (US); Priscilla Brebi-Mieville, Pitrufquen (CL)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/634,318

(22) PCT Filed: Mar. 11, 2011

(86) PCT No.: PCT/US2011/028045
§ 371 (c)(1),
(2), (4) Date: Jan. 9, 2013

(87) PCT Pub. No.: WO2011/112901
PCT Pub. Date: Sep. 15, 2011

(65) Prior Publication Data
US 2013/0109584 A1 May 2, 2013

Related U.S. Application Data

(60) Provisional application No. 61/313,422, filed on Mar. 12, 2010.

(51) Int. Cl.
C40B 30/04 (2006.01)
C12Q 1/68 (2006.01)

(52) U.S. Cl.
CPC ........ *C12Q 1/6886* (2013.01); *C12Q 2600/154* (2013.01); *C12Q 1/6869* (2013.01); *C12Q 2600/106* (2013.01); *C12Q 2600/156* (2013.01)
USPC ............................................................. 506/9

(58) Field of Classification Search
None
See application file for complete search history.

(56) References Cited

U.S. PATENT DOCUMENTS

2009/0264306 A1* 10/2009 Caldwell et al. .................. 506/9

OTHER PUBLICATIONS

Dehn, D., et al., "Human papillomavirus testing and molecular markers of cervical dysplasia and carcinoma", Cancer, (2007), vol. 111, No. 1, pp. 1-14.
Beaudenon, S., et al., "HPV E6, E6AP and cervical cancer", BMC Biochem, (2008), 9 Suppl I: p. S4.
Schorge, J., et al., "P16 as a molecular biomarker of cervical adenocarcinoma", Am J Obstet Gynecol, (2004), vol. 190, No. 3, pp. 668-673.
Tringler, B., et al., "Evaluation of p16INK4a and pRb expression in cervical squamous and glandular neoplasia", Hum Pathol, (2004), vol. 35, No. 6, pp. 689-696.
Wentzensen, N., et al., "Utility of methylation markers in cervical cancer early detection: appraisal of the state-of-the-science", Gynecol Oncol, (2009), vol. 112, No. 2, pp. 293-299.
Shivapurkar, N., et al., "Evaluation of candidate methylation markers to detect cervical neoplasia", Gynecol Oncol, (2007), vol. 107, No. 3, pp. 549-553.
Esteller, M., "Epigenetics in cancer", N Engl J Med, (2008), vol. 358, No. 11, pp. 1148-1159.
Vucic, E., et al., "Methylation analysis by DNA immunoprecipitation (MeDIP)", Methods Mol Biol, (2009), vol., pp. 141-153.
Apostolidou, S., et al., "DNA methylation analysis in liquid-based cytology for cervical cancer screening", Int J Cancer, (2009), vol. 125, No. 12, pp. 2995-3002.
Hogue, M., et al., "Genome-wide genetic characterization of bladder cancer: a comparison of high-density single-nucleotide polymorphism arrays and PCR-based microsatellite analysis", Cancer Res, (2003), vol. 63, No. 9, pp. 2216-2222.
Van Den Brule, A., et al., "GPS+/6+ PCR followed by reverse line blot analysis enables rapid and high-throughput identification of human papillomavirus genotypes", J Clin Microbiol, (2002), vol. 40, No. 3, pp. 779-787.
Scacheri, P., et al., "Statistics for ChIP-chip and DNase hypersensitivity experiments on NimbleGen arrays", Methods Enzymol, (2006), vol. 411, pp. 270-282.
Herman, J., et al., "Methylation-specific PCR: a novel PCR assay for methylation status of CpG islands", Proc Natl Acad Sci USA, (1996), vol. 93, No. 18, pp. 9821-9826.
Rodenhiser, D., et al., "Epigenetic mapping and functional analysis in a breast cancer metastasis model using whole-genome promoter tiling microarrays", Breast Cancer Res, (2008), vol. 10, No. 4, pp. R62.
Mulero-Navarro, S., et al., "Epigenetic biomarkers for human cancer: The time is now", Crit Rev Oncol Hematol, (2008), vol. 68, pp. 1-11.
Fleischer, T., et al., "Identification and characterization of three new components of the mSin3A corepressor complex", Mol Cell Biol, (2003), vol. 23, No. 10, pp. 3456-3467.

(Continued)

*Primary Examiner* — Jennifer McDonald
*Assistant Examiner* — Valerie Toodle
(74) *Attorney, Agent, or Firm* — Johns Hopkins Technology Transfer

(57) ABSTRACT

Pap smears and HPV infection tests do not distinguish between lesions that will progress to an invasive carcinoma and those that will not. We aimed to identify epigenetic biomarkers for diagnosis and progression monitoring of premalignant lesions in cervical cancer. Hypermethylated genes were identified as potential biomarkers after validation by MSP, including GGTLA4 and ZNF516. The methylation frequency for these two genes was higher in tumor: GGTLA4 (100%) and ZNF516 (96%); than in normal samples: GGTLA4 (12%) and ZNF516 (16%). The methylation status of GGTLA4 showed a progression in methylation frequency from normal samples to invasive carcinoma. The immunohistochemical expression was lower in tumor for both: GGTLA4 (50.8%) and ZNF516 (66.2%); than in normal samples: GGTLA4 (71.2%) and ZNF516 (88.1%) (p<0.05). In conclusion, we identified methylation biomarkers for the molecular screening and characterization of cervical cancer.

7 Claims, 7 Drawing Sheets

(56) References Cited

OTHER PUBLICATIONS

Baillat, D., et al., "Integrator, a multiprotein mediator of small nuclear RNA processing, associates with the C-terminal repeat of RNA polymerase II", Cell, (2005), vol. 123, No. 2, pp. 265-276.
Gebhard, C., et al., "Genome-wide profiling of CpG methylation identifies novel targets of aberrant hypermethylation in myeloid leukemia", Cancer Res, (2006), vol. 66, No. 12, pp. 6118-6128.
Jacinto, F., et al., "Discovery of epigenetically silenced genes by methylated DNA immunoprecipitation in colon cancer cells", Cancer Res, (2007), vol. 67, No. 24, pp. 11481-11486.
Jacinto, F., et al., "Methyl-DNA immunoprecipitation (MeDIP): hunting down the DNA methylome", Biotechniques, (2008), vol. 44, No. 1, pp. 35, 37, 39 passim.
Jin, S., et al., "Examination of the specificity of DNA methylation profaling techniques towards S-methylcytosine and S-hydroxymethylcytosine", Nucleic Acids Res, (2010), vol. 38, No. 11, pp. e125.
Movassagh, M., et al., "Differential DNA methylation correlates with differential expression of angiogenic factors in human heart failure", PLoS One, (2010), vol. 5, No. 1, pp. e8564.
Weber, M., et al., "Chromosome-wide and promoter-specific analyses identify sites of differential DNA methylation in normal and transformed human cells", Nat Genet, (2005), vol. 37, No. 8, pp. 853-862.
Kron, K. et al., "Discovery of novel hypermethylated genes in prostate cancer using genomic CpG island microarrays", PLoS One, (2009), vol. 4, No. 3, pp. e4830.
Lai, H., et al., "Identification of novel DNA methylation markers in cervical cancer", Int J Cancer, (2008), vol. 123, No. 1, pp. 161-167.
Yamashita, K, et al., "Pharmacologic unmasking of epigenetically silenced tumor suppressor genes in esophageal squamous cell carcinoma", Cancer Cell, (2002), vol. 2, No. 6, pp. 485-495.
Jones, P., et al., "Cancer epigenetics comes of age", Nat Genet, (1999), vol. 21, No. 2, pp. 163-167.
Herman, J., et al., "Gene silencing in cancer in association with promoter hypermethylation", N Engl J Med, (2003), vol. 349, No. 21, pp. 2042-2054.
Espada, J., et al., "DNA methylation and the functional organization of the nuclear compartment", Semin Cell Dev Biol, (2010), vol. 21, No. 2, pp. 238-246.
Hoque, M., et al., "Genome-wide promoter analysis uncovers portions of the cancer methylome", Cancer Res, (2008), vol. 68, No. 8, pp. 2661-2670.
Yamashita, K, et al., "HOP/OBI/NECCI promoter DNA is frequently hypermethylated and involved in tumorigenic ability in esophageal squamous cell carcinoma", Mol Cancer Res, (2008), vol. 6, No. 1, pp. 31-41.
Runowicz, C., "Molecular screening for cervical cancer—time to give up Pap tests?", N Engl J Med, (2007), vol. 357, No. 16, pp. 1650-1653.
Ault, K., "Epidemiology and natural history of human papillomavirus infections in the female genital tract", Infect Dis Obstet Gynecol, 2006 Suppl, p. 40470.
Chan, J., et al., "Impact of the human papilloma vaccine on cervical cancer", J Clin Oncol, (2007), vol. 25, No. 20, pp. 2975-2982.
Boulet, G.A., et al., "Human papillomavirus in cervical cancer screening: important role as biomarker", Cancer Epidemiol Biomarkers Prev, (2008), vol. 17, No. 4, pp. 810-817.
Lie, A., et al., "Human papillomavirus E6/E7 mRNA testing as a predictive marker for cervical carcinoma", Expert Rev Mol Diagn, (2008), vol. 8, No. 4, pp. 405-415.
Murphy, N., et al., "p16INK4A, CDC6, and MCMS: predictive biomarkers in cervical preinvasive neoplasia and cervical cancer", J Clin Pathol, (2005), vol. 58, No. 5, pp. 525-534.
Melsheimer, P., et al., "DNA aneuploidy and integration of human papillomavirus type 16 e6/e7 oncogenes in intraepithelial neoplasia and invasive squamous cell carcinoma of the cervix uteri", Clin Cancer Res, (2004), vol. 10, No. 9, pp. 3059-3063.
Kruse, A., et al., "Evaluation of MIB-1 positive cell clusters as a diagnostic marker for cervical intraepithelial neoplasia", Am J Surg Pathol, (2002), vol. 26, No. 11., pp. 1501-1507.
Ault, K., et al., "Telomerase activity as a potential diagnostic marker for triage of abnormal Pap smears", J Low Gerrit Tract Dis, (2005), vol. 9, No. 2, pp. 93-99.
Yang, J., "FLIP as an anti-cancer therapeutic target", Yonsei Med J, (2008), vol. 49, No. 1, pp. 19-27.
Nees, M., et al., "Identification of novel molecular markers which correlate with HPV-induced tumor progression", Oncogene, (1998), vol. 16, No. 19, pp. 2447-2458.
Unger, E., et al., "Molecular markers for early detection of cervical neoplasia" Dis Markers, (2004), vol. 20, No. 2, pp. 103-116.
Wang, K, et al., "Field methylation silencing of the protocadherin 10 gene in cervical carcinogenesis as a potential specific diagnostic test from cervical scrapings", Cancer Sci, (2009) vol. 100, No. 11, pp. 2175-2180.
Overmeer, R., et al., "Repression of MAL tumour suppressor activity by promoter methylation during cervical carcinogenesis", Journal of Pathology, (2009), vol. 219, No. 3, pp. 327-336.
Cheng, H., et al., "DNA methylation and carcinogenesis of PRDM5 in cervical cancer", J Cancer Res Clin Oncol, (2010), vol. 136, No. 3, pp. 1821-1825.
Iliopoulos, D., et al., "Correlation of promoter hypermethylation in hTERT, DAPK and MGMT genes with cervical oncogenesis progression", Oncology reports, (2009), vol. 22, No. 1, pp. 199-204.
Giacinti, L., et al., "Epigenome: a new target in cancer therapy", Clin Ter, (2008), vol. 159, No. 5, pp. 347-360.
Weng, Y., et al., "Methylated DNA immunoprecipitation and microarray-based analysis: detection of DNA methylation in breast cancer cell lines", Methods Mol Biol, (2009), vol. 590, pp. 165-176.

* cited by examiner

FIG. 1

```
                          SEQUENCE LISTING

<160> NUMBER OF SEQ ID NOS: 42

<210> SEQ ID NO 1
<211> LENGTH: 25
<212> TYPE: DNA
<213> ORGANISM: Artificial Sequence
<220> FEATURE:
<223> OTHER INFORMATION: amplification primers

<400> SEQUENCE: 1
gtgtttaggg tttttgttt ttttt                                         25

<210> SEQ ID NO 2
<211> LENGTH: 25
<212> TYPE: DNA
<213> ORGANISM: Artificial Sequence
<220> FEATURE:
<223> OTHER INFORMATION: amplification primers

<400> SEQUENCE: 2
aaccactcac ctaaatcatc ttctc                                        25

<210> SEQ ID NO 3
<211> LENGTH: 21
<212> TYPE: DNA
<213> ORGANISM: Artificial Sequence
<220> FEATURE:
<223> OTHER INFORMATION: amplification primers

<400> SEQUENCE: 3
gaggtttgtt tgtagaggtt c                                            21

<210> SEQ ID NO 4
<211> LENGTH: 24
<212> TYPE: DNA
<213> ORGANISM: Artificial Sequence
<220> FEATURE:
<223> OTHER INFORMATION: amplification primers

<400> SEQUENCE: 4
caaaacaact ctaaaaaaat tttc                                         24

<210> SEQ ID NO 5
<211> LENGTH: 21
<212> TYPE: DNA
<213> ORGANISM: Artificial Sequence
<220> FEATURE:
<223> OTHER INFORMATION: amplification primers

<400> SEQUENCE: 5 ataggggag tttaagtaag g                                             21

<210> SEQ ID NO 6
<211> LENGTH: 21
<212> TYPE: DNA
<213> ORGANISM: Artificial Sequence
<220> FEATURE:
<223> OTHER INFORMATION: amplification primers

<400> SEQUENCE: 6
```

```
ccacttaacc caaatacccc c                                              21
```

<210> SEQ ID NO 7
<211> LENGTH: 26
<212> TYPE: DNA
<213> ORGANISM: Artificial Sequence
<220> FEATURE:
<223> OTHER INFORMATION: amplification primers

<400> SEQUENCE: 7

```
gttttaaaag tgttttttttt gtgttt                                        26
```

<210> SEQ ID NO 8
<211> LENGTH: 24
<212> TYPE: DNA
<213> ORGANISM: Artificial Sequence
<220> FEATURE:
<223> OTHER INFORMATION: amplification primers

<400> SEQUENCE: 8

```
gaactctaaa actacaaaaa ccac                                           24
```

<210> SEQ ID NO 9
<211> LENGTH: 21
<212> TYPE: DNA
<213> ORGANISM: Artificial Sequence
<220> FEATURE:
<223> OTHER INFORMATION: amplification primers

<400> SEQUENCE: 9

```
ttgagtatga tggggtatgt g                                              21
```

<210> SEQ ID NO 10
<211> LENGTH: 22
<212> TYPE: DNA
<213> ORGANISM: Artificial Sequence
<220> FEATURE:
<223> OTHER INFORMATION: amplification primers

<400> SEQUENCE: 10

```
ccctactaat aacaaataac tc                                             22
```

<210> SEQ ID NO 11
<211> LENGTH: 22
<212> TYPE: DNA
<213> ORGANISM: Artificial Sequence
<220> FEATURE:
<223> OTHER INFORMATION: amplification primers

<400> SEQUENCE: 11

```
gagtgttgtt ggtagattgt tg                                             22
```

<210> SEQ ID NO 12
<211> LENGTH: 23
<212> TYPE: DNA
<213> ORGANISM: Artificial Sequence
<220> FEATURE:
<223> OTHER INFORMATION: amplification primers

<400> SEQUENCE: 12

```
ctataaacaa taccaaacct cac                                            23
```

<210> SEQ ID NO 13
<211> LENGTH: 24
<212> TYPE: DNA
<213> ORGANISM: Artificial Sequence

```
<220> FEATURE:
<223> OTHER INFORMATION: amplification primers

<400> SEQUENCE: 13 tttttggaa tttaagggtt ttac                                              24

<210> SEQ ID NO 14
<211> LENGTH: 22
<212> TYPE: DNA
<213> ORGANISM: Artificial Sequence
<220> FEATURE:
<223> OTHER INFORMATION: amplification primers

<400> SEQUENCE: 14
gttggttggg ttgagtatta tt                                               22

<210> SEQ ID NO 15
<211> LENGTH: 27
<212> TYPE: DNA
<213> ORGANISM: Artificial Sequence
<220> FEATURE:
<223> OTHER INFORMATION: amplification primers

<400> SEQUENCE: 15
gttttgtttt ttatattttt gtttttg                                          27

<210> SEQ ID NO 16
<211> LENGTH: 20
<212> TYPE: DNA
<213> ORGANISM: Artificial Sequence
<220> FEATURE:
<223> OTHER INFORMATION: amplification primers

<400> SEQUENCE: 16
caacctcccc ctacccaaac                                                  20

<210> SEQ ID NO 17
<211> LENGTH: 24
<212> TYPE: DNA
<213> ORGANISM: Artificial Sequence
<220> FEATURE:
<223> OTHER INFORMATION: amplification primers

<400> SEQUENCE: 17
tttggggttg ttgaaagaaa ttat                                             24

<210> SEQ ID NO 18
<211> LENGTH: 23
<212> TYPE: DNA
<213> ORGANISM: Artificial Sequence
<220> FEATURE:
<223> OTHER INFORMATION: amplification primers

<400> SEQUENCE: 18
caaactttta aataactcct ccc                                              23

<210> SEQ ID NO 19
<211> LENGTH: 19
<212> TYPE: DNA
<213> ORGANISM: Artificial Sequence
<220> FEATURE:
<223> OTHER INFORMATION: amplification primers

<400> SEQUENCE: 19
gggaggggtg ggttgattc                                                   19
```

```
<210> SEQ ID NO 20
<211> LENGTH: 19
<212> TYPE: DNA
<213> ORGANISM: Artificial Sequence
<220> FEATURE:
<223> OTHER INFORMATION: amplification primers

<400> SEQUENCE: 20 gctaaccccca ctcaccccc                                                   19

<210> SEQ ID NO 21
<211> LENGTH: 26
<212> TYPE: DNA
<213> ORGANISM: Artificial Sequence
<220> FEATURE:
<223> OTHER INFORMATION: amplification primers

<400> SEQUENCE: 21
tttttttttg tagttttatt tatagc                                            26

<210> SEQ ID NO 22
<211> LENGTH: 25
<212> TYPE: DNA
<213> ORGANISM: Artificial Sequence
<220> FEATURE:
<223> OTHER INFORMATION: amplification primers

<400> SEQUENCE: 22
ccaaaatcac taaaaaaaaa caaac                                             25

<210> SEQ ID NO 23
<211> LENGTH: 22
<212> TYPE: DNA
<213> ORGANISM: Artificial Sequence
<220> FEATURE:
<223> OTHER INFORMATION: amplification primers

<400> SEQUENCE: 23
tacgacggtg aggtacgtat ac                                                22

<210> SEQ ID NO 24
<211> LENGTH: 25
<212> TYPE: DNA
<213> ORGANISM: Artificial Sequence
<220> FEATURE:
<223> OTHER INFORMATION: amplification primers

<400> SEQUENCE: 24
caaaaacaca aaaataatac tcgaa                                             25

<210> SEQ ID NO 25
<211> LENGTH: 25
<212> TYPE: DNA
<213> ORGANISM: Artificial Sequence
<220> FEATURE:
<223> OTHER INFORMATION: amplification primers

<400> SEQUENCE: 25
gtatgatggt gaggtatgta tatga                                             25

<210> SEQ ID NO 26
<211> LENGTH: 25
<212> TYPE: DNA
<213> ORGANISM: Artificial Sequence
<220> FEATURE:
<223> OTHER INFORMATION: amplification primers
```

<400> SEQUENCE: 26
caaaaacaca aaataatac tcaaa                                    25

<210> SEQ ID NO 27
<211> LENGTH: 25
<212> TYPE: DNA
<213> ORGANISM: Artificial Sequence
<220> FEATURE:
<223> OTHER INFORMATION: amplification primers

<400> SEQUENCE: 27
ttacgtgttt tattatgttt cgtgc                                   25

<210> SEQ ID NO 28
<211> LENGTH: 23
<212> TYPE: DNA
<213> ORGANISM: Artificial Sequence
<220> FEATURE:
<223> OTHER INFORMATION: amplification primers

<400> SEQUENCE: 28
gaaaaaacac tcatcgtttc gtt                                     23

<210> SEQ ID NO 29
<211> LENGTH: 25
<212> TYPE: DNA
<213> ORGANISM: Artificial Sequence
<220> FEATURE:
<223> OTHER INFORMATION: amplification primers

<400> SEQUENCE: 29
atgtgtttta ttatgttttg tgtgt                                   25

<210> SEQ ID NO 30
<211> LENGTH: 23
<212> TYPE: DNA
<213> ORGANISM: Artificial Sequence
<220> FEATURE:
<223> OTHER INFORMATION: amplification primers

<400> SEQUENCE: 30
aaaaaaacac tcatcatttc att                                     23

<210> SEQ ID NO 31
<211> LENGTH: 23
<212> TYPE: DNA
<213> ORGANISM: Artificial Sequence
<220> FEATURE:
<223> OTHER INFORMATION: amplification primers

<400> SEQUENCE: 31
ttggatatta aagggtgatt ttc                                     23

<210> SEQ ID NO 32
<211> LENGTH: 22
<212> TYPE: DNA
<213> ORGANISM: Artificial Sequence
<220> FEATURE:
<223> OTHER INFORMATION: amplification primers

<400> SEQUENCE: 32
ccgtaatcct acaaaccta cg                                       22

<210> SEQ ID NO 33

```
<211> LENGTH: 24
<212> TYPE: DNA
<213> ORGANISM: Artificial Sequence
<220> FEATURE:
<223> OTHER INFORMATION: amplification primers

<400> SEQUENCE: 33
ttggatatta aagggtgat tttt                                          24

<210> SEQ ID NO 34
<211> LENGTH: 25
<212> TYPE: DNA
<213> ORGANISM: Artificial Sequence
<220> FEATURE:
<223> OTHER INFORMATION: amplification primers

<400> SEQUENCE: 34
ttccataatc ctacaaaccc tacat                                        25

<210> SEQ ID NO 35
<211> LENGTH: 24
<212> TYPE: DNA
<213> ORGANISM: Artificial Sequence
<220> FEATURE:
<223> OTHER INFORMATION: amplification primers

<400> SEQUENCE: 35
cgttagttaa tagacgggag gttc                                         24

<210> SEQ ID NO 36
<211> LENGTH: 23
<212> TYPE: DNA
<213> ORGANISM: Artificial Sequence
<220> FEATURE:
<223> OTHER INFORMATION: amplification primers

<400> SEQUENCE: 36
ctaaatacta cgcccaataa ccg                                          23

<210> SEQ ID NO 37
<211> LENGTH: 26
<212> TYPE: DNA
<213> ORGANISM: Artificial Sequence
<220> FEATURE:
<223> OTHER INFORMATION: amplification primers

<400> SEQUENCE: 37
tgtgttagtt aatagatggg aggttt                                       26

<210> SEQ ID NO 38
<211> LENGTH: 25
<212> TYPE: DNA
<213> ORGANISM: Artificial Sequence
<220> FEATURE:
<223> OTHER INFORMATION: amplification primers

<400> SEQUENCE: 38
cctaaatact acacccaata accac                                        25

<210> SEQ ID NO 39
<211> LENGTH: 22
<212> TYPE: DNA
<213> ORGANISM: Artificial Sequence
<220> FEATURE:
<223> OTHER INFORMATION: amplification primers

<400> SEQUENCE: 39
```

```
cgaaggggtt gttagtagta gc                                        22

<210> SEQ ID NO 40
<211> LENGTH: 23
<212> TYPE: DNA
<213> ORGANISM: Artificial Sequence
<220> FEATURE:
<223> OTHER INFORMATION: amplification primers

<400> SEQUENCE: 40
aaacaaaaaa aataaccgac gat                                       23

<210> SEQ ID NO 41
<211> LENGTH: 25
<212> TYPE: DNA
<213> ORGANISM: Artificial Sequence
<220> FEATURE:
<223> OTHER INFORMATION: amplification primers

<400> SEQUENCE: 41
gtgaaggggt tgttagtagt agtgt                                     25

<210> SEQ ID NO 42
<211> LENGTH: 26
<212> TYPE: DNA
<213> ORGANISM: Artificial Sequence
<220> FEATURE:
<223> OTHER INFORMATION: amplification primers

<400> SEQUENCE: 42
aaaaaacaaa aaaataacc aacaat                                     26
```

HYPERMETHYLATION BIOMARKERS FOR DETECTION OF CERVICAL CANCER

CROSS-REFERENCE TO RELATED APPLICATIONS

This application is a 35 U.S.C. 371 U.S. national entry of International Application PCT/US2011/028045, having an international filing date of Mar. 11, 2011, which claims the benefit of U.S. Provisional Application No. 61/313,422, filed Mar. 12, 2010, the content of each of the aforementioned applications is herein incorporated by reference in their entirety.

STATEMENT OF GOVERNMENTAL INTEREST

This invention was made with government support under grant no. U01 CA84986 awarded by the National Institutes of Health. The government has certain rights in the invention.

TECHNICAL FIELD OF THE INVENTION

This invention is related to the area of cervical cancer. In particular, it relates to detection and characterization of cervical cancer.

BACKGROUND OF THE INVENTION

Cervical cancer (CC), the second most prevalent cancer in women and the fifth cause of death by cancer among women worldwide is a considerable public health problem[1]. Around 470,000 new cases of cervical cancer are detected annually, mostly in developing nations, of which approximately half will die [2].

Cervical cancer is a cellular alteration that originates in the epithelium of the cervix and is initially apparent through slow and progressively evolving precursor lesions that can occur in various stages of cervical intraepithelial neoplasia (CIN), grouped into low and high-grade squamous intraepithelial lesions (LSIL and HSIL respectively). These lesions could evolve into cancer in situ (circumscribed to the epithelial surface) and/or invasive cancer once they have crossed over to the basal membrane of the epithelium [3]. The alteration in cell cycle control mediated by human papilloma virus (HPV) oncoproteins is the main molecular mechanism of action in cervical cancer [4-6]. HPV infection is very common and is present almost in 80% of women with an active sexual life [7]. The most frequently involved HPV genotype in these lesions is HPV 16, which can be observed in LSIL, HSIL and cancer, as well as in normal cytology [8-12]. Although oncogenic HPV is necessary for the transformation of cervical-epithelial cells, it is not a sufficient cause, and a variety of cofactors and molecular events influence whether cervical cancer will develop[13].

While cytological screening and HPV infection tests has substantially reduced cervical cancer incidence and mortality where it has been successfully implemented, it is limited by low single-test sensitivity and poor reproducibility for equivocal and minor abnormalities [14, 15].

Biomarkers that identify key molecular events involved in the initiation and progression of cervical cancer, regardless of etiologic co-factors, may prove to be useful for screening, diagnostic and clinical management purposes in both resource rich and developing countries. Epigenomic biomarkers may prove to be useful early detection, diagnostic and progression markers for cervical carcinoma[16]. DNA hypermethylation, the best understood epigenomic biomarker in cancer research, leads to changes in gene expression which accumulate during oncogenic progression and are potentially reversible [17]. Gene-specific DNA hypermethylation is an effective transcription silencing mechanism, which is more frequent than the gene inactivation produced by mutations or other genetic changes seen in cancer [18].

Studies on animals and humans have confirmed that promoter hypermethylation is also often present in the precursor lesions of a variety of cancers [17]. As a result, these changes could be used as diagnostic biomarkers for cervical neoplasia, either alone or in combination with cytology and HPV tests.

There is a continuing need in the art for means of diagnosing, characterizing, and monitoring cervical cancers.

SUMMARY OF THE INVENTION

One aspect of the invention is a method for identifying uterine cervical cancer in a human. Epigenetic silencing of at least one gene selected from the group consisting of GGTLA4, FKBP6, ZNF516, SAP130, and INTS1 is tested for in a test sample containing uterine cervical cells or nucleic acids from uterine cervical cells. The test sample is identified as containing cells that are neoplastic or as containing nucleic acids from cells that are neoplastic upon detection of the epigenetic silencing.

Another aspect of the invention is a kit for assessing uterine cervical cancer in a test sample containing uterine cervical cells or nucleic acids from uterine cervical cells. The kit comprises in a package: a reagent that (a) modifies methylated cytosine residues but not non-methylated cytosine residues, or that (b) modifies non-methylated cytosine residues but not methylated cytosine residues; and at least one pair of oligonucleotide primers that specifically hybridizes under amplification conditions to a region of a gene selected from the group consisting of GGTLA4, FKBP6, ZNF516, SAP130, and INTS1; wherein the region is within about 1 kb of said gene's transcription start site; and instructions for assessing uterine cervical cancer using the reagents.

Another aspect of the invention is a kit for assessing uterine cervical cancer in a test sample containing cervical cells or nucleic acids from cervical squamous cells. The kit comprises in a package: at least two pairs of oligonucleotide primers that specifically hybridize under amplification conditions to a region of a gene selected from the group consisting of GGTLA4, FKBP6, ZNF516, SAP130, and INTS1; wherein the region is within about 1 kb of said gene's transcription start site; and instructions for assessing uterine cervical cancer using the primers.

Yet another aspect of the invention is a method for characterizing a uterine cervical cancer in a human. A test sample containing uterine cervical cells or nucleic acids from uterine cervical cells is tested for epigenetic silencing of at least one gene selected from the group consisting of GGTLA4, FKBP6, ZNF516, SAP130, and INTS1. The presence, amount, or absence of said epigenetic silencing characterizes the test sample.

These and other embodiments which will be apparent to those of skill in the art upon reading the specification provide the art with methods and tools for assessment of clinical samples for the presence or amount of cancer cells or nucleic acids.

BRIEF DESCRIPTION OF THE DRAWINGS

FIG. 1. Bisulfite sequencing candidate genes in the same samples used to hybridize microarrays. The figure represents CpG methylation density in the promoter regions. Bisulfite sequence analysis results are summarized as filled circles representing methylated CpGs and open circles representing unmethylated CpGs. (The figure shows only the first seven cytocines of the fragment, in six representative samples of the population).

FIG. 3C: FKBP6 (M137, U135 bp), FIG. 3D: ZNF516 (M 241, U 242 bp), FIG. 3E: INTS1 (M 143, U 147 bp)

FIG. 4A: GGTLA4, FIG. 4B: FKBP6, FIG. 4C: ZNF516, FIG. 4D: INTS1 and FIG. 4E: SAP130.

FIG. 5A: Top functional categories and FIG. 5B: canonical pathways from our data set based on significance. The human pathway lists determined by "Ingenuity System Database" in related cervical samples.

FIG. 6A: GGTLA4, FIG. 6B: FKBP6, FIG. 6C: ZNF516 and FIG. 6D: INTS1.

FIG. 7A: GGTLA4, FIG. 7B: FKBP6, FIG. 7C: ZNF516 and FIG. 7D: INTS1. * p-value <0.05.

DETAILED DESCRIPTION OF THE INVENTION

Figure 2:
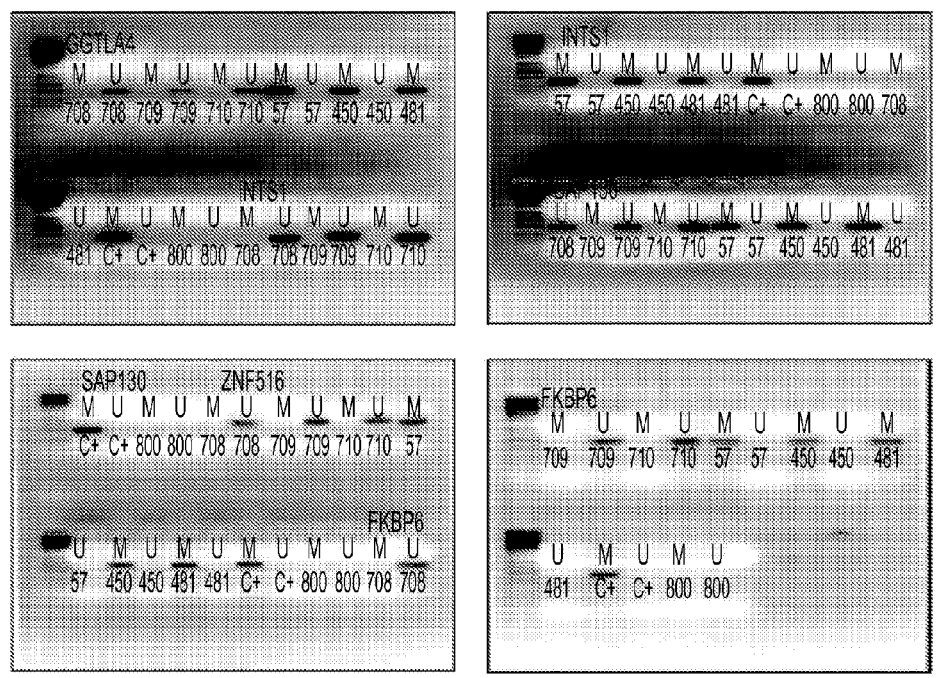
FIG. 2. Methylation Specific PCR (MSP) results in the samples that were hybridized to the microarrays. M: Methylated, U: Unmethylated; Positive Control (C+) 100% Methylated Bisulfite treated DNA (ZymoResearch); Negative Control (C−) PCR product without DNA (blank). (Samples #708-710 Normal; #57-481 Tumor).
Figure 3A:
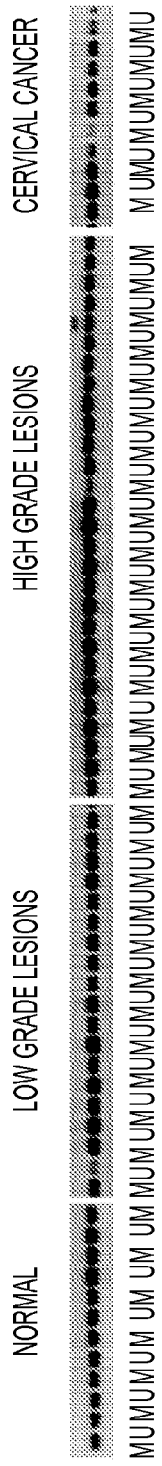
FIGS. 3A-3E. Methylation Specific PCR (MSP) results for FIG. 3A: β-actin (268 bp), FIG. 3B:GGTLA4 (M183, U185 bp)
Figure 3B:
Figure 3C:
Figure 3D:
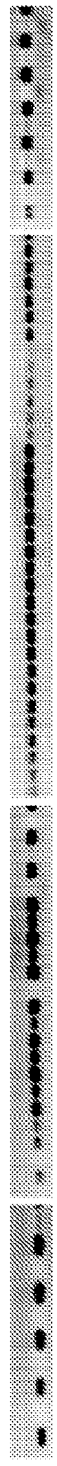
Figure 3E:
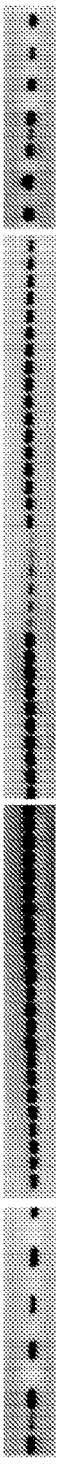
Figure 3F:
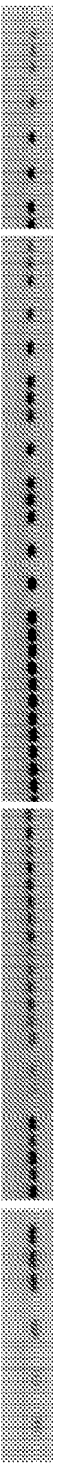
FIG. 3F: SAP130 (M 189, U 192 bp) by histology type. M: Methylated, U: Unmethylated.
Figure 4A:
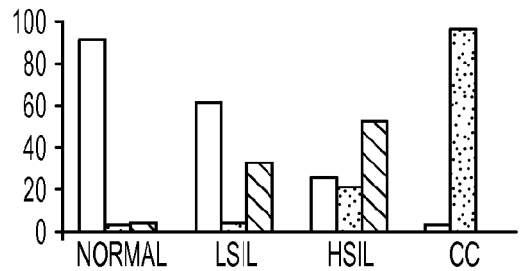
FIGS. 4A-4E. Methylation frequency bargraphs by histology type: Normal, LSIL (Low Squamous Intraepithelial Lesions), HSIL (High Squamous Intraepithelial Lesions) and CC (Tumor).
Figure 4B:
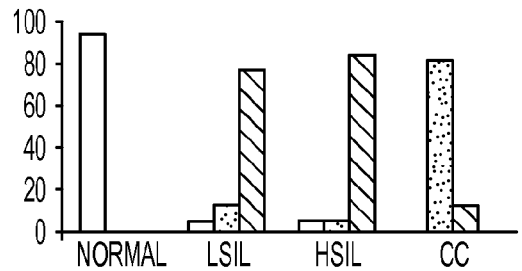
Figure 4C:
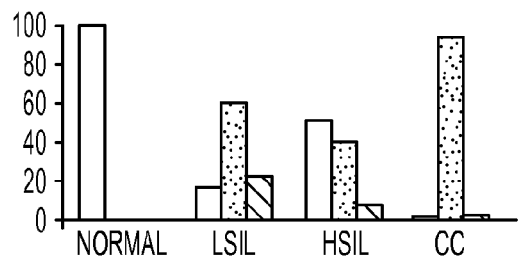
Figure 4D:
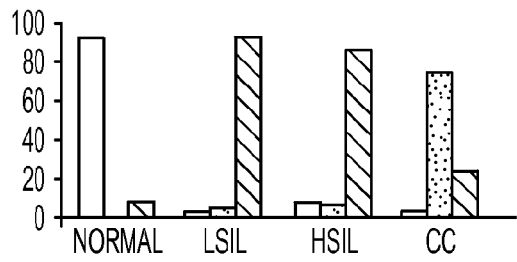
Figure 4E:
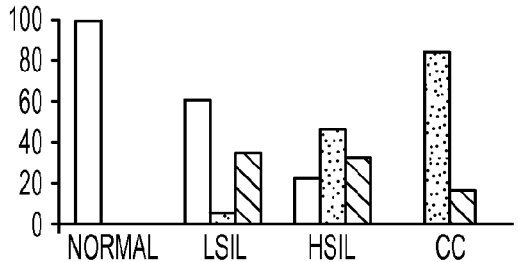

The inventors have developed a set of biomarkers that can be used alone or in combinations to assess the presence of uterine cervical cancer. While the inventors do not intend to be bound by any theories of mechanism of action, the biomarkers which are hypermethylated and hypoexpressed in cancer cells may be tumor suppressors. We used Methylated DNA immunoprecipitation (MeDIP) chip, an unbiased and high-throughput method, to detect novel differentially methylated candidate genes for cervical cancer diagnosis. These genes may be used as biomarkers, by themselves and in combination with HPV infection cervical cytology readings, for diagnosis and disease progression monitoring of premalignant lesions in cervical cancer [19, 20]

Because of the heterogeneity of tumors from individual to individual, even tumors of the same organ or type, any single marker may not yield sufficient sensitivity. Thus it may be beneficial to use panels of markers to increase the sensitivity of detection. One particular panel of markers that may be used for detection of cervical carcinoma comprises GGTLA4 and ZNF516.

Tests can be carried out on any suitable sample that is likely to yield cervical cells or their nucleic acids. Particular samples which can be used include tissue specimens, biopsy specimens, surgical specimens, cervical swabs, and cytological specimens. It may be beneficial to extract nucleic acids from the cells prior to testing. Some techniques of testing may not require pre-extraction. Some testing may be done on proteins which may or may not be extracted from the cells prior to testing for particular detection techniques.

Any tests can be used to detect either hypermethylation, hypoexpression, or both. Suitable tests which can be used without limitation include lab-on-chip technology, microfluidic technologies, biomonitor technology, proton recognition technologies (e.g., Ion Torrent), and other highly parallel and/or deep sequencing methods. Once a biomarker is known as epigenetically silenced, either hypermethylation or hypoexpression may be used as in indicator of silencing.

Epigenetic modification of a gene can be determined by any method known in the art. One method is to determine that a gene which is expressed in normal cells or other control cells is less expressed or not expressed in tumor cells, i.e., hypoexpressed or silenced. This method does not, on its own, however, prove that the silencing or activation is epigenetic, as the mechanism of the silencing or inactivation could be genetic, for example, by somatic mutation. One method to determine that silencing is epigenetic is to treat with a reagent, such as DAC (5'-deazacytidine), or with a reagent which changes the histone acetylation status of cellular DNA or any other treatment affecting epigenetic mechanisms present in cells, and observe that the silencing is reversed, i.e., that the expression of the gene is reactivated or restored. Another means to determine epigenetic modification is to determine the presence of methylated CpG dinucleotide motifs in the silenced gene or the absence of methylation CpG dinucleotide motifs in an activated gene. Typically these methylated motifs reside near the transcription start site, for example, within about 3 kbp, within about 2.5 kbp, within about 2 kbp, within about 1.5 kbp, within about 1 kbp, within about 750 bp, or within about 500 bp. Once a gene has been identified as the target of epigenetic modification in tumor cells, determination of reduced or enhanced expression can be used as an indicator of epigenetic modification.

Expression of a gene can be assessed using any means known in the art. Typically expression is assessed and compared in test samples and control samples which may be normal, non-malignant cells. The test samples may contain cancer cells or pre-cancer cells or nucleic acids from them. Samples will desirably contain cervical cells. Samples may contain mixtures of different types and stages of cancer cells. Either mRNA (or cDNA) or protein can be measured to detect expression which may be used as an indicator of epigenetic modification. Methods employing hybridization to nucleic acid probes can be employed for measuring specific mRNAs. Such methods include using nucleic acid probe arrays (microarray technology), in situ hybridization, and using Northern blots. Messenger RNA can also be assessed using amplification techniques, such as RT-PCR. Advances in genomic technologies now permit the simultaneous analysis of thousands of genes, although many are based on the same concept of specific probe-target hybridization. Sequencing-based methods are an alternative; these methods may be based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest.

Specific proteins can be assessed using any convenient method including immunoassays, immunohistochemistry, and immunocytochemistry, but are not limited to that. Most such methods will employ antibodies which are specific for the particular protein or protein fragments. The sequences of the mRNA (cDNA) and proteins of the markers of the present invention are known in the art and publicly available.

Methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Examples of the former are Acc III, Ban I, BstN I, Msp I, and Xma I. Examples of the latter are Acc II, Ava I, BssH II, BstU I, Hpa II, and Not I. Alternatively, chemical reagents can be used which selectively modify either the methylated or non-methylated form of CpG dinucleotide motifs.

Modified products can be detected directly, or after a further reaction which creates products which are easily distinguishable. Means which detect altered size and/or charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it. Bisulfite ion-treated DNA can be treated with alkali. Other means which rely on specific sequences can be used, including but not limited to hybridization, amplification, sequencing, and ligase chain reaction, Combinations of such techniques can be uses as is desired.

The principle behind electrophoresis is the separation of nucleic acids via their size and charge. Many assays exist for detecting methylation and most rely on determining the presence or absence of a specific nucleic acid product. Gel electrophoresis is commonly used in a laboratory for this purpose.

One may use MALDI mass spectrometry in combination with a methylation detection assay to observe the size of a nucleic acid product. The principle behind mass spectrometry is the ionizing of nucleic acids and separating them according to their mass to charge ratio. Similar to electrophoresis, one can use mass spectrometry to detect a specific nucleic acid that was created in an experiment to determine methylation.

One form of chromatography, high performance liquid chromatography, is used to separate components of a mixture based on a variety of chemical interactions between a substance being analyzed and a chromatography column. DNA is first treated with sodium bisulfite, which converts an unmethylated cytosine to uracil, while methylated cytosine residues remain unaffected. One may amplify the region containing potential methylation sites via PCR and separate the products via denaturing high performance liquid chromatography (DHPLC). DHPLC has the resolution capabilities to distinguish between methylated (containing cytosine) and unmethylated (containing uracil) DNA sequences.

Hybridization is a technique for detecting specific nucleic acid sequences that is based on the annealing of two complementary nucleic acid strands to form a double-stranded molecule. One example of the use of hybridization is a microarray assay to determine the methylation status of DNA. After sodium bisulfite treatment of DNA, which converts an unmethylated cytosine to uracil while methylated cytosine residues remain unaffected, oligonucleotides complementary to potential methylation sites can hybridize to the bisulfite-treated DNA. The oligonucleotides are designed to be complimentary to either sequence containing uracil (thymine) or sequence containing cytosine, representing unmethylated and methylated DNA, respectively. Computer-based microarray technology can determine which oligonucleotides hybridize with the DNA sequence and one can deduce the methylation status of the DNA. Similarly primers can be designed to be complimentary to either sequence containing uracil (thymine) or sequence containing cytosine. Primers and probes that recognize the converted methylated form of DNA are dubbed methylation-specific primers or probes (MSP).

An additional method of determining the results after sodium bisulfite treatment involves sequencing the DNA to directly observe any bisulfite-modifications. Pyrosequencing technology is a method of sequencing-by-synthesis in real time. It is based on an indirect bioluminometric assay of the pyrophosphate (PPi) that is released from each deoxynucleotide (dNTP) upon DNA-chain elongation. This method presents a DNA template-primer complex with a dNTP in the presence of an exonuclease-deficient Klenow DNA polymerase. The four nucleotides are sequentially added to the reaction mix in a predetermined order. If the nucleotide is complementary to the template base and thus incorporated, PPi is released. The PPi and other reagents are used as a substrate in a luciferase reaction producing visible light that is detected by either a luminometer or a charge-coupled device. The light produced is proportional to the number of nucleotides added to the DNA primer and results in a peak indicating the number and type of nucleotide present in the form of a pyrogram. Pyrosequencing can exploit the sequence differences that arise following sodium bisulfate-conversion of DNA.

A variety of amplification techniques may be used in a reaction for creating distinguishable products. Some of these techniques employ PCR. Other suitable amplification methods include the ligase chain reaction (LCR) (Barringer et al, 1990), transcription amplification (Kwoh et al. 1989; WO88/10315), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO90/06995), nucleic acid based sequence amplification (NASBA) (U.S. Pat. Nos. 5,409,818; 5,554,517; 6,063,603), microsatellite length polymorphism (MLP), and nick displacement amplification (WO2004/067726).

Sequence variation that reflects the methylation status at CpG dinucleotides in the original genomic DNA offers two approaches to PCR primer design. In the first approach, the primers do not themselves "cover" or hybridize to any potential sites of DNA methylation; sequence variation at sites of differential methylation are located between the two primers. Such primers are used in bisulfate genomic sequencing, COBRA, Ms-SNuPE. In the second approach, the primers are designed to anneal specifically with either the methylated or unmethylated version of the converted sequence. If there is a sufficient region of complementarity, e.g., 12, 15, 18, or 20 nucleotides, to the target, then the primer may also contain additional nucleotide residues that do not interfere with hybridization but may be useful for other manipulations. Exemplary of such other residues may be sites for restriction endonuclease cleavage, for ligand binding or for factor binding or linkers or repeats. The oligonucleotide primers may or may not be such that they are specific for modified methylated residues One way to distinguish between modified and unmodified DNA is to hybridize oligonucleotide primers which specifically bind to one form or the other of the DNA. After hybridization, an amplification reaction can be performed and amplification products assayed. The presence of an amplification product indicates that a sample hybridized to the primer. The specificity of the primer indicates whether the DNA had been modified or not, which in turn indicates whether the DNA had been methylated or not. For example, bisulfite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulfite-modified DNA, whereas an oligonucleotide primer containing the guanine bases would hybridize to the non-modified (methylated) cytosine residues in the DNA. Amplification using a DNA polymerase and a second primer yield amplification products which can be readily observed. Such a method is termed MSP (Methylation Specific PCR; U.S. Pat. Nos. 5,786,146; 6,017, 704; 6,200,756). The amplification products can be optionally hybridized to specific oligonucleotide probes which may also be specific for certain products. Alternatively, oligonucleotide probes can be used which will hybridize to amplification products from both modified and nonmodified DNA.

Another way to distinguish between modified and non-modified DNA is to use oligonucleotide probes which may also be specific for certain products. Such probes can be hybridized directly to modified DNA or to amplification products of modified DNA. Oligonucleotide probes can be labeled using any detection system known in the art. These include but are not limited to fluorescent moieties, radioisotope labeled moieties, bioluminescent moieties, luminescent moieties, chemiluminescent moieties, enzymes, substrates, receptors, or ligands.

Still another way for the identification of methylated CpG dinucleotides utilizes the ability of the MBD domain of the McCP2 protein to selectively bind to methylated DNA sequences (Cross et al, 1994; Shiraishi et al, 1999). Restriction endonuclease digested genomic DNA is loaded onto expressed His-tagged methyl-CpG binding domain that is immobilized to a solid matrix and used for preparative column chromatography to isolate highly methylated DNA sequences.

Real time chemistry allows for the detection of PCR amplification during the early phases of the reactions, and makes quantitation of DNA and RNA easier and more precise. A few variations of the real-time PCR are known. They include the TaqMan™ (Roche Molecular Systems) system and Molecular Beacon™ system which have separate probes labeled with a fluorophore and a fluorescence quencher. In the Scorpion™ system the labeled probe in the form of a hairpin structure is linked to the primer. In addition, the Amplifluor™ (Chemicon International) system and the Plexor™ (Promega) system can be used.

DNA methylation analysis has been performed successfully with a number of techniques which include the MALDI-TOFF, MassARRAY, MethyLight, Quantitative analysis of ethylated alleles (QAMA), enzymatic regional methylation assay (ERMA), HeavyMethyl, QBSUPT, MS-SNuPE, MethylQuant, Quantitative PCR sequencing, and Oligonucleotide-based microarray systems.

The number of genes whose modification is tested and/or detected can vary: one, two, three, four, five, or more genes can be tested and/or detected. In some cases at least two genes are selected. In other embodiments at least three genes are selected.

Testing can be performed diagnostically or in conjunction with a therapeutic regimen. Testing can be used to monitor efficacy of a therapeutic regimen, for example, a chemotherapeutic agent or a biological agent, such as a polynucleotide. Testing can also be used to determine what therapeutic or preventive regimen to employ on a patient. Moreover, testing can be used to stratify patients into groups for testing agents and determining their efficacy on various groups of patients. Such uses characterize the cancer into categories based on the genes which are epigenetically silenced and/or the amount of silencing of the genes. In the case of a diagnosis or characterization, information comprising data or conclusions can be written or communicated electronically or orally. The identification may be assisted by a machine. Communication of the data or conclusions may be from a clinical laboratory to a clinical office, from a clinician to a patient, or from a specialist to a generalist, as examples. The form of communication of data or conclusions typically may involve a tangible medium or physical human acts.

A test sample obtainable from tissue or cell specimens or fluids includes detached tumor cells and/or free nucleic acids that are released from dead or damaged tumor cells. Nucleic acids include RNA, genomic DNA, mitochondrial DNA, single or double stranded, and protein-associated nucleic acids: Any nucleic acid specimen in purified or non-purified form obtained from such specimen cell can be utilized as the starting nucleic acid or acids. The test samples may contain cancer cells or pre-cancer cells or nucleic acids from them.

Demethylating agents can be contacted with cells in vitro or in vivo for the purpose of restoring normal gene expression to the cell or for validation of methylation. Suitable demethylating agents include, but are not limited to 5-aza-2'-deoxycytidine, 5-aza-cytidine, Zebularine, procaine, and L-ethionine. This reaction may be used for diagnosis, for determining predisposition, and for determining suitable therapeutic regimes.

Although diagnostic and prognostic accuracy and sensitivity may be achieved by using a combination of markers, such as 5 or 6 markers, or 9 or 10 markers, practical considerations may dictate use of smaller combinations. Any combination of markers for a specific cancer may be used which comprises 2, 3, 4, or 5 markers. Combinations of 2, 3, 4, or 5 markers can be readily envisioned given the specific disclosures of individual markers provided herein.

Kits according to the present invention are assemblies of reagents for testing methylation and/or silencing. They are typically in a package which contains all elements, optionally including instructions. Instructions may be in any form, including paper or digital. The instructions may be on the inside or the outside of the package. The instructions may be in the form of an internet address which directs one to a description of or demonstration of the detailed manipulative or analytic techniques. The package may be divided so that components are not mixed until desired. Components may be in different physical states. For example, some components may be lyophilized and some in aqueous solution. Some may be frozen. Individual components may be separately packaged within the kit. The kit may contain reagents, as described above for differentially modifying methylated and non-methylated cytosine residues. Desirably the kit will contain oligonucleotide primers which specifically hybridize to regions within 1 kb of the transcription start sites of the selected genes/biomarkers. Additional markers may be used. Typically the kit will contain both a forward and a reverse primer for a single gene or marker. If there is sufficient region of complementarity, e.g., 12, 15, 18, or 20 nucleotides, then the primer may also contain additional nucleotide residues that do not interfere with hybridization but may be useful for other manipulations. Exemplary of such other residues may be sites for restriction endonuclease cleavage, for ligand binding or for factor binding or linkers or repeats. The oligonucleotide primers may or may not be such that they are specific for modified methylated residues. The kit may optionally contain oligonucleotide probes. The probes may be specific for sequences containing modified methylated residues or for sequences containing non-methylated residues. The kit may optionally contain reagents for modifying methylated cytosine residues. The kit may also contain components for performing amplification, such as a DNA polymerase (particularly a thermostable DNA polymerase) and deoxyribonucleotides, labeled or not. Means of detection may also be provided in the kit, including detectable labels on primers or probes. Kits may also contain reagents for detecting gene expression. Such reagents may include probes, primers, or antibodies, for example. In the case of enzymes or ligands, substrates or binding partners may be used to assess the presence of the marker. Kits may contain 1, 2, 3, 4, or more of the primers or primer pairs of the invention. Kits that contain probes may have them as separate molecules or covalently linked to a primer for amplifying the region to which the probes hybridize. Other useful tools for performing the methods of the invention or associated testing, therapy, or calibration may also be included in the kits, including buffers, enzymes, gels, plates, detectable labels, vessels, etc. Kits may include tools for collecting suitable samples, such as tools for collecting a uterine cervical swab.

As an example, a gene may be contacted with hydrazine, which modifies cytosine residues, but not methylated cytosine residues. Then the hydrazine-treated gene sequence may be contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding non-methylated gene sequence, gaps are apparent at positions in the test gene contained methylated cytosine residues. The presence of gaps is indicative of methylation of a cytosine residue in the CpG dinucleotide in the target gene of the test cell.

Bisulfite ions, for example, sodium bisulfite, convert non-methylated cytosine residues to bisulfite modified cytosine residues. The bisulfite ion treated gene sequence can be exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. The sulfonate group can be removed by exposure to alkaline conditions, resulting in the formation of uracil. The DNA can be amplified, for example, by PCR, and sequenced to determine whether CpG sites are methylated in the DNA of the sample. Uracil is recognized as a thymine by Taq polymerase and, upon PCR, the resultant product contains cytosine only at the position where 5-methylcytosine was present in the starting template DNA. One can compare the amount or distribution of uracil residues in the bisulfite ion treated gene sequence of the test cell with a similarly treated corresponding non-methylated gene sequence. A decrease in the amount or distribution of uracil residues in the gene from the test cell indicates methylation of cytosine residues in CpG dinucleotides in the gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

The use of hypermethylated genes as biomarkers is advantageous because, the changes in the DNA methylation state and chromatin modifications are characteristic of neoplastic cells, which is why these different patterns can be useful in diagnosing and classifying tumors[27]. We have identified five novel methylation markers for cervical cancer with the use of MeDIP and unbiased promoter methylation arrays. These genes (FKBP6, SAP130, INTS1, GGTLA4, and ZNF516) may be useful tools for the diagnosis, categorization, and progression monitoring of cervical cancer. The GGTLA4 protein is one of the members of the gamma-glutamyl transpeptidase (GGT) family, which is important in the metabolism of glutathione. The FKBP6 protein is a member of the immunophilin protein family, which plays a role in immuno-regulation and basic cellular processes involving protein folding and trafficking[28]. The SAP130 protein is a subunit of the histone deacetylase dependent SIN3A co-repressor complex [29]. The INTS1 protein is a subunit of the Integrator complex, which associates with the C-terminal domain of RNA polymerase II large subunit and mediates 3-prime end processing of small nuclear RNAs U1 and U2 [30]. ZNF516 is zinc finger protein 516. This protein showed significant methylation in leukemia confirmed by down-regulation in leukemia cell lines [31].

We identify novel methylated genes in cervical tissues by hybridizing MeDIP enriched DNA to Nimblegen 385K CpG Islands plus Promoter methylation arrays (MeDIP-chip). The genes identified as differentially methylated with the promoter arrays were subsequently validated in normal samples, precancerous lesions and malignancy. Many other genes may be discovered using similar approaches or different selection criteria. MeDIP in combination with microarray technology or other novel high-throughput strategies suits the need for high-resolution analysis of the hypermethylome. The application of MeDIP combined to hybridization with microarrays is used for the discovery of new biomarkers in cancer cells and other pathologies[32-35]. Weber et al., used MeDIP for the first time, revealed the usefulness of this technique for obtaining high-resolution maps of the human methylome [36]. The MeDIP-chip approach has already been shown to be useful in identifying differentially methylated genes in colon and prostate cancer [32, 37]. MeDIP is a genome-wide, high-resolution approach to detect DNA methylation. The method utilizes a monoclonal antibody specific for 5 mC to immuno-precipitate DNA containing highly methylated CpG sites. Immuno-captured DNA is purified, labeled and hybridized to oligonucleotide tiling arrays or used for high-throughput sequencing. MeDIP is a fast and simple approach, used to determine DNA methylation on a genome-wide scale and to compare DNA methylation patterns between two samples with diversely different DNA methylation status [38]. A simplified high throughput MeDIP-chip assay will enable translational research studies in clinics and populations, which will greatly enhance our understanding of the human methylome in cancer and other pathologies. [33-35]

The cancer epigenome has great potential in clinical diagnosis and therapeutic intervention [39]. Many genes modified by promoter hypermethylation have classic tumor-suppressor function. Examples are the VHL gene in renal cancer, the cell-cycle-control gene p16 in many types of cancer, and the mismatch repair gene MLH1 in colorectal cancer and other neoplasms [40]. According to Knudsen's hypothesis, two hits are required to inactivate both alleles of a tumor suppressor gene and promote tumorigenesis[41]. These can occur by deletion, mutation or methylation[42]. The number of cancer-related genes affected by epigenetic inactivation equals or exceeds the number that are inactivated by mutation[43]. Studies in mammals have linked patterns of DNA methylation to gene expression: methylation in a gene promoter region generally correlates with a silenced gene[43]. There are three models that could explain the transcriptional silencing induced by DNA methylation. The first assumes that CpG methylation per se inhibits the binding of sequence-specific transcription factors to their binding sites in the chromatin fiber [44]. In the second model CpG methylation has a direct effect on nucleosome positioning by promoting the assembly of specialized nucleosome structures that can directly repress gene transcription[45]. In the third model DNA methylation promotes the recruitment to specific sites in the chromatin fiber of nuclear factors that recognize methylated CpG dinucleotides and either impede the binding of other nuclear factors to target sites or have a direct effect on repressing transcription[44].

Our data show a decrease in expression in ZNF516 and GGTLA4 (p<0.05). This may be due to the fact that our study evaluated only a small part of the promoter region of the genes, ZNF516 (241 bp), FKBP6 (137 bp), GGTLA4 (183 bp), SAP130 (189 bp) and INTS1 (143 bp), and a high percentage of the CpG islands need to be methylated for there to be a loss in expression (50%) [43, 46].

Detection of HPV DNA and the Pap test are already available for uterine cervical cancer screening. The Pap test has limitations, especially its limited sensitivity, estimated at only 51%, which results in the need for additional cervical cytologic tests at regular intervals[48]. HPV testing has been shown to have greater sensitivity than the Pap test in randomized trials for the detection of cervical intraepithelial neoplasia [15]. However, combined Pap and HPV testing does not distinguish between lesions that will progress to an invasive carcinoma. Methylation markers may be another useful tool for screening or diagnostic purposes that can be added to currently available cervical cancer screening and characterization algorithms. The MSP methylation detection in the genes GGTLA4, ZNF516, FKBP6 INTS1 and SAP130 has greater sensitivity (94.90%-100%) and specificity (88.00%-100.0%) for the detection of cervical neoplasia. SAP130 conferred the best performance with sensitivities of 100% and specificities of 100% for SCC. Our results support the use of genome-wide technologies for identifying novel diagnostic, prognostic, theranostics, and therapeutic targets in cancer research, specifically cervical cancer. Our results revealed that four genes, GGTLA4, ZNF516, SAP130 and FKBP6 have a higher correlation (1.00 and 0.90) with cancer status than HPV (0.80). However, HPV AUC were lower than FKBP6 (0.98), SAP130 (1.00), and ZNF516 (1.00).

The high rate of HPV infection, mainly in adolescence, and its unquestionable association with CC led to the need to create a vaccine [49-51]. There are currently two prophylactic vaccines on the market Gardasil™ (Merck) and Cervarix™ (GlaxoSmithKline) [50, 52, 53]. It protects against the main viral types involved in CCU (HPV 16 and 18) [50, 52, 53]. Both vaccines have a high rate of effectiveness and they generate a good immune response, protecting against 100% of the infections produced by the viral types covered [53, 54]. Despite that, these vaccines have some disadvantages, such as their cost and not having much effect on those already infected. Another factor to consider is that the vaccine has only been in use during the last 5 years, and at this point it is not possible to know how long the immunity will last in those vaccinated [54]. More important still, the current vaccines do not cover all the oncogenic HPV types; they only cover HPV 16 and 18, which are found in 70% of CC. Therefore approximately 30% of cervical cancer tumors will not be prevented with the vaccines, even assuming universal coverage and perfect utilization. Thus, women may become infected with other high-risk viral types and must continue to obtain PAP tests in the future. On the other hand, HPV vaccination will further reduce the efficiency of cytological screening. Therefore, new screening modalities need to be evaluated and pursued[14].

Several novel cervical cancer biomarkers have been recently proposed. Viral oncoproteins E6 and E7 messenger RNA (mRNA) levels may be useful prognosis indicator in patients with HPV-associated cervical cancer[55]. Detection of over-expression of the protein $p16^{INK4a}$ is a sensitive and specific marker of high-risk oncogenic HPV infection-associated cervical lesions in precancerous and cancerous cervical tissue. Detection of over-expression of $p16^{INK4a}$ measured with immunohistochemistry has high sensitivity and specificity in the identification of CIN II lesions [56]. CDC6 has been shown to be over-expressed in high-grade lesions and advanced cancer [57]. Another group of proposed biomarkers determine chromosomal instability by measuring aneuploidy due to its role in neoplastic transformation [58] and viral integration for its correlation with the viral physical state and the state of progression [59]. Several proliferation biomarkers have also been proposed: KI67 (strongly expressed protein in the CIN and normal tissue that maintain proliferation capacity) [60], MYC (over-expressed in advanced stages of cancer) [60], cyclins (over-expressed in cancer and pre-neoplastic lesions) [61], telomerase (facilitates the immortality of cells in most types of cancer and displays a differential expression between cancerous and normal cells) [62] and c-FLIP (over-expressed in advanced stages of cancer) [63]. There are few studies on biomarkers of progression in cervical carcinogenesis, within them are the study of the ubiquity of DNA methylation changes as novel biomarkers for early cancer detection and risk prediction has opened the way to a host of innovative diagnostic and prognostic treatment strategies[20]. Also the study of two genes, C4.8 and C21.7, are of particular interest because their expression is up-regulated in a subset of high-grade precancerous lesions and in over 58% of cancers. These two genes may therefore be considered as putative progression markers [64]. Nishimura et al., studied the role of genetic instability and LOH (loss of heterozygosity) in the progression of cervical cancer and also to analyze for correlations between these genetic abnormalities and the clinicopathologic characteristics of cervical cancers obtaining that the LOH at 3p is an early event [65].

In summary, we identified new methylation biomarkers that hold promise for the molecular screening, monitoring, and characterization of uterine cervical cancer. The utility of methylation biomarkers in conjunction with HPV testing warrants further investigation in different ethnic and geographic backgrounds [39, 55]. More comprehensive prospective population-based studies using a standardized methylation assay may be used to translate these methylated DNA sequences into commercial cancer biomarkers [39]. Moreover, the reported results can be validated in a larger population-based screening sample.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Methods
Materials and Methods
Clinical samples: The samples were collected at Doctor Hernán Henríquez Aravena (HHHA) tertiary care regional hospital in Temuco, Chile, between 2004-2008. The diagnosis was confirmed by histological examination (biopsy) during which a team of three pathologists from HHHA read the results and achieved a consensus diagnosis. A random set of pathology slides from the study samples was sent for diagnostic and immunohistochemistry confirmatory review by a pathologist at Johns Hopkins School of Medicine. The protocol for this study was approved by the Institutional Review Boards (IRB) of the Hernan Henríquez Aravena Hospital and the Johns Hopkins School of Medicine. To determinate the methylation status of promoter regions in the genome, 12 normal samples and 7 cervical cancers were used to perform the hybridization to an oligonucleotide tiling array (385K CpG Islands plus Promoter arrays, Nimblegen, Wis.). MSP validation was performed on 221 HPV genotyped samples: 25 normal, 66 Low Grade Lesions (LSIL), 91 High Grade Lesions (HSIL) and 39 cervical cancers (CC). Normal, LSIL, HSIL and 18% of cancer samples were collected with cytobrush. Tumor tissue (82%) was also collected at the operating room after tumor removal and fixed in paraffin. Immunohistochemistry analysis was performed on 122 samples assembled in tissue microarrays (TMAs): 59 normal and 63 CC.

DNA extraction: Tissue was digested with 1% SDS and 50 µg/mL proteinase K (Boehringer Mannheim) at 48° C. overnight, followed by phenol/chloroform extraction and ethanol precipitation of DNA as previously described [21]. The integrity of extracted DNA was verified by a PCR amplification of a 268-bp fragment of the β-globin gene using GH20 and PCO4 primers.

HPV genotyping: HPV detection and genotyping were performed as previously described [22]. Briefly, HPV detection was achieved by amplification of the L1 fragment using GP5+ and biotin GP6+ primers. Reverse Line Blot (RLB) analysis was performed using modified oligoprobes (oncogenic: 16, 18, 26, 31, 33, 35, 39, 45, 51, 52, 53, 56, 58, 59, 66, 68, 73, 82, subtypes IS39 and W13B/MM4 and non-oncogenic: 6, 11, 34, 40, 42, 43, 44, 54, 55, 57, 61, 70, 71, 72, 81, 83, 84 and CP6108 HPVs) for the analysis. A panel of 36 HPV viral types was used as positive control. HPV 16, 18, 31 and 33 were commercial plasmid clones (ATCC) and the remaining HPV types were provided by Dr. Peter Snijders (VU University Medical Center, Amsterdam, The Netherlands). Negative controls consisted of commercial genomic DNA (Promega, Madison, Wis.) and deionised water.

MeDIP enrichment and promoter methylation microarray hybridization: The MagMeDIP kit (Diagenode) was used to enrich the DNA with methylated cytosines according to manufacturer's protocol. Genomic DNA (500 ng) was sheared using a water bath sonicator (Bioruptor UCD-200, Diagenode) at "LOW" power setting in the following cycles: (alternating 5 minutes sonication and 2 minutes on ice) for a total sonication time of 15 minutes. Sonicated DNA was then analyzed on a 1.5% agarose gel to ensure that sonicated fragments had an optimal size of 200-1000 bp. Sonicated DNA was denatured for 10 min at 95° C. and immunoprecipitated with monoclonal antibody against 5-methylcytidine. A separate fraction of sonicated input genomic DNA was amplified and purified with the GenomePlex® Complete Whole Genome Amplification (WGA) Kit (Sigma-Aldrich) and the QIAquick PCR Purification Kit (Qiagen). Immunoprecipitated methylated DNA (2 µg) was labeled with Cy5 fluorophere and the input genomic DNA was labeled with Cy3 fluorophere. Labeled DNA from the enriched and the input pools were combined and hybridized to the 385K Human CpG Island-Plus-PromoterArray (Roche-NimbleGen), which represents 28K UCSC-annotated CpG islands and promoter regions for 17K RefSeq genes from the HG18 build.

The standard Nimblegen algorithms were used to compute the normalized data and identify peaks of enrichment, coinciding with methylated regions. Next the data was transformed into a more usable format, i.e. the peaks near known transcription start sites (TSSs) were identified, according to 2 different cutoffs for the maximal distance between a peak and a TSS:

−1000 to +1000, called the standard cutoff
−500 to +500, called the narrow cutoff In a first pass analysis, the cancer specifically hypermethylated genes were identified, i.e. those genes that are methylated in at least one of the primary cancer samples and in none of the normal samples. To maximize the amount of informative loci, this condition was set at a slightly more stringent level positive methylated in 20% or more of the cancer cases. Practically, this is equivalent to at least 2 methylated samples out of a total of 7. A third more stringent criteria was also used setting the level at 100% positive methylated cases in cancer and none in normal.

The Nimblegen protocol identified 255 unique genes that are cancer specifically methylated according to the standard cutoff, 189 according to the narrow cutoff and 10 according to the most stringent criteria. The most interesting and cancer specific set of genes were identified, i.e. no methylation in any of the 12 normals and methylation in all of the 7 tumors over a broad area, from −1000 to +1000 relative to TSS.

The methylation peak scores for each probe in the methylation arrays were calculated and ranked using the ACME algorithm [23]. Loci with ratios >2.0 were accepted as hypermethylated. The genes selected for biomarker validation were hypermethylated in all tumor microarrays and had the highest methylation peak scores in cancer (>2.0).

Bisulfite conversion: Genomic DNA (1 ug) was bisulfite converted with the Epitect Bisulfite kit (Qiagen), according to the manufacturer's instruction sand stored at −80° C. Bisulfite conversion was confirmed by amplification of a 280-bp fragment of the β-actin gene using the Forward (GTGTT-TAGGGTTTTTTGTTTTTTTT; SEQ ID NO:1), and Reverse (AACCACTCACCTAAATCATCTTCTC; SEQ ID NO:2) primers.

Bisulfite genomic sequence analysis: Bisulfite sequence analysis (BS) was done to determine the methylation status in normal and tumor tissues used in the microarrays. Bisulfite-treated DNA was amplified for the 5' region that included at least a portion of the CpG island within 1 kb of the proposed transcriptional start site using bisulfite sequencing primer sets (Table 1). The primers for bisulfite sequencing were designed to hybridize to regions in the promoter without CpG dinucleotides. PCR products were gel-purified using the QIAquick Gel Extraction Kit (Qiagen) according to the manufacturer's instructions. Each amplified DNA sample was sequenced by the Applied Biosystems 3700 DNA analyzer using nested, forward, or reverse primers and BD terminator dye (Applied Biosystems).

TABLE 1

Primer list of genes used for bisulfite sequencing.

| GENE NAME | FORWARD 5'→3' | REVERSE 3'→5' |
|---|---|---|
| GGTLA4 | GAGGTTTGTTTGTAGAGGTTC (SEQ ID NO: 3) | CAAAACAACTCTAAAAAAATTTTC (SEQ ID NO: 4) |
| CGB5 | ATAGGGGGAGTTTAAGTAAGG (SEQ ID NO: 5) | CCACTTAACCCAAATACCCCC (SEQ ID NO: 6) |
| FKBP6 | GTTTTAAAAGTGTTTTTTTTGTGTTT (SEQ ID NO: 7) | GAACTCTAAAACTACAAAAACCAC (SEQ ID NO: 8) |
| TRIM74 | TTGAGTATGATGGGGTATGTG (SEQ ID NO: 9) | CCCTACTAATAACAAATAACTC (SEQ ID NO: 10) |
| ZNF516 | GAGTGTTGTTGGTAGATTGTTG (SEQ ID NO: 11) | CTATAAACAATACCAAACCTCAC (SEQ ID NO: 12) |
| MICAL-L2 | TTTTTTGGAATTTAAGGGTTTTAC (SEQ ID NO: 13) | GTTGGTTGGGTTGAGTATTATT (SEQ ID NO: 14) |
| ZAP701 | GTTTGTTTTTATATTTTGTTTTTG (SEQ ID NO: 15) | CAACCTCCCCCTACCCAAAC (SEQ ID NO: 16) |
| RGS12 | TTTGGGGTTGTTGAAAGAAATTAT (SEQ ID NO: 17) | CAAACTTTTAAATAACTCCTCCC (SEQ ID NO: 18) |
| SAP130 | GGGAGGGGTGGGTTGATTC (SEQ ID NO: 19) | GCTAACCCCACTCACCCCC (SEQ ID NO: 20) |
| INTS1 | TTTTTTTTTGTAGTTTTATTTATAGC (SEQ ID NO: 21) | CCAAAATCACTAAAAAAAAACAAAC (SEQ ID NO: 22) |

Methylation specific PCR (MSP): MSP primers were designed to amplify DNA Methylated (M) and/or unmethylated (U). Primers were designed to specifically amplify the promoters of the genes of interest (see the website at the urogene.org domain, the methprimer subdomain, and the index page). Primer sequences and annealing temperatures are provided in Table 2. Briefly, bisulfate-modified DNA was used as template for methylation specific PCR (MSP), as previously described [24]. We used 100% Methylated Bisulfite treated DNA (ZymoResearch) as positive controls. The PCR products were analyzed by electrophoresis on 1.5% agarose gels and visualized after ethidium bromide staining. The candidate genes were validated using MSP in a two stage approach: In the first stage an internal validation was performed in the 19 samples that were hybridized to the array; in the second stage the genes were validated in the 221 study participants. A gene was scored as methylated when we observed a band after amplification with the methylated primers and the intensity of the methylated band was higher that the unmethylated band. A gene was scored as unmethylated when we observed a band after amplification with the unmethylated primers and the intensity of the unmethylated band was higher that the methylated band. A gene was scored as partially methylated when were observed both bands methylated and unmethylated with the same intensity. A gene was scored as unmethylated when we observed a band after amplification with the unmethylated primers and the intensity of the unmethylated band was higher that the methylated band. A gene was scored as partially methylated when were observed both bands methylated and unmethylated with the same intensity.

TABLE 2

Methylation Specific PCR (MSP) primers

| Gene Name | Forward | Reverse | Product (bp) | Tm (° C.) |
|---|---|---|---|---|
| ZNF516 | M TACGACGGTGAGGTACGTATAC (SEQ ID NO: 23) | CAAAAACACAAAAATAATACTCGAA (SEQ ID NO: 24) | 241 | 54.2 |
| ZNF516 | U GTATGATGGTGAGGTATGTATATGA (SEQ ID NO: 25) | CAAAAACACAAAAATAATACTCAAA (SEQ ID NO: 26) | 242 | 50 |
| FKBP6 | M TTACGTGTTTTATTATGTTTCGTGC (SEQ ID NO: 27) | GAAAAAACACTCATCGTTTCGTT (SEQ ID NO: 28) | 137 | 58 |
| FKBP6 | U ATGTGTTTTATTATGTTTTGTGTGT (SEQ ID NO: 29) | AAAAAAACACTCATCATTTCATT (SEQ ID NO: 30) | 135 | 54 |
| GGTLA4 | M TTGGATATTAAAGGGTGATTTTC (SEQ ID NO: 31) | CCGTAATCCTACAAACCCTACG (SEQ ID NO: 32) | 183 | 55 |

TABLE 2-continued

Methylation Specific PCR (MSP) primers

| Gene Name | Forward | Reverse | Product (bp) | Tm (° C.) |
|---|---|---|---|---|
| GGTLA4 | U TTGGATATTAAAGGGGTGATTTTT (SEQ ID NO: 33) | TTCCATAATCCTACAAACCCTACAT (SEQ ID NO: 34) | 185 | 52.5 |
| SAP130 | M CGTTAGTTAATAGACGGGAGGTTC (SEQ ID NO: 35) | CTAAATACTACGCCCAATAACCG (SEQ ID NO: 36) | 189 | 52.5 |
| SAP130 | U TGTGTTAGTTAATAGATGGGAGGTTT (SEQ ID NO: 37) | CCTAAATACTACACCCAATAACCAC (SEQ ID NO: 38) | 192 | 55 |
| INTS1 | M CGAAGGGGTTGTTAGTAGTAGC (SEQ ID NO: 39) | AAACAAAAAAAATAACCGACGAT (SEQ ID NO: 40) | 143 | 55 |
| INTS1 | U GTGAAGGGGTTGTTAGTAGTAGTGT (SEQ ID NO: 41) | AAAAAACAAAAAAAATAACCAACAAT (SEQ ID NO: 42) | 147 | 52 |

Immunohistochemical staining: Immunohistochemistry (IHQ) was performed to identify the differential distribution and localization of expressed proteins for GGTLA4, INTS1, FKBP6, and ZNF516 in a separate cohort of 59 normal cervical mucosa samples and 63 cervical carcinoma tissue samples which were mounted on tissue microarrays. Paraffin sections of tissue microarrays were mounted on xylene-coated slides, dewaxed, rehydrated, and incubated for 15 minutes with 3% hydrogen peroxide to block endogenous peroxidase activity. The antigenic sites were unmasked by heating in a steamer for 30 minutes in 0.01 M citrate buffer. The sections were incubated for 1 hour in the dark with antibodies for FKBP6 (Abcam, Cambridge, USA), ZNF516 (Sigma Aldrich, St. Louis, USA), INTS1 (Sigma Aldrich St. Louis, USA) and GGTLA4 (GenWay, San Diego, USA) diluted in Tris buffer. Sections were then rinsed in Tris buffer and incubated at room temperature with Envision (Dako, Glastrup, Denmark) 1:2 Tris buffer as a secondary antibody for 30 minutes in the dark. Slides were developed using 3-3' diaminobenzidine as the chromogen.

The IHQ staining was scored in a semi-quantitative fashion by taking both, the percentage of positive nuclear staining and intensity of staining into account. Tissue microarrays were evaluated for immunoreactivity by three surgical pathologists from the Hernan Henríquez Aravena Hospital and subsequently confirmed by a surgical pathologist at Johns Hopkins School of Medicine. The IHQ staining score was obtained by the addition of staining intensity (negative=0; weak=1; moderate=2; strong=3) and the percentage of positive cells (negative=0; 1-25%=1; 26-50%=2; 51-75%=3; >75%=4). IHQ staining was considered negative when the final score was 0 and positive staining when the final score was 1, 2 or 3.

Statistical Analyses: Univariable and bivariable analysis was performed to examine the association between DNA hypermethylation and age, socio-economic status and ethnic group. Correlations and Receiver Operator Curves [25] were calculated to examine the association between DNA methylation and disease status. Specificity, sensitivity and Area Under the Curve of each hypermethylated gene was estimated to examine the usefulness of these epigenomic alterations as biomarkers for diagnosis and disease progression. The sensitivities were defined as (the number of positive testing results in SCC/the total number of SCC) and the specificity as (the number of negative testing results in Normal/the total number of Normal). Chi square tests were employed to conduct comparative analysis of variables. All analysis was performed using the Stata program, version 11.0. Results were considered statistically significant if the P-value was <0.05.

EXAMPLE 2

Characteristics of the Patients

Two groups of patients were used in this study: One for the MSP validation (A) and other one for the IHQ analysis (B). Clinical and demographic variables were different in cases patients (LSIL, HSIL and CC) and controls. The age of the patients into three groups:<30 years (A:22.6%, B:10.7%), 30-50 years (A:54.8%, B:39.3%) and >50 years (A:22.6%, B:50.0%). Both groups of samples the lesion status was associated with age as expected. In the group A the most of low grade lesions (63.6%) were seen in patients <30 years old. High grade lesions were mostly seen (94.3%) among 31-50 year old patients, and 97.4% of invasive carcinoma patients were >50 years old. In the group B normal patients were mostly seen (40.7%) among 31-50 year old patients, and 61.9% of invasive carcinoma patients were >50 years old. The ethnic descent of the patients was divided between native Chilean people (Mapuche) (A:22.2%, B: 28.7%) and Hispanic European (A:77.8%, B: 71.3%). The majority of the samples came from patients that were not Mapuches. The patients are all public assistance patients who receive different amounts of health care subsidy according to their income level. The sample was divided into three socio-economic groups within this subgroup of the population: Indigent (A:55.2%, B: 46.7%), Income level ≤US$ 310 (A:29.4%, B: 39.3%), and Income level >US$ 310 (A:15.4%, B: 13.9%). The income level of the patients from whom sample was taken is relatively low compared to the average income in Chile, since these are patients who receive medical attention in the public system (Table 3 and 6).

EXAMPLE 3

HPV Genotyping.

PCR and Reverse line blot analyses revealed that 176 (79.6%) samples were HPV positive and 45 (20.4%) were HPV negative. Among normal samples 12% were HPV positive, most for single infection of HPV 16. Among LSIL 82% were HPV positive, most with single infections with HPV16 (41%) or HPV 11 (9%). Among the HPV positive LSIL lesions, 14% were multiple infections, most with HPV 16 and 18. Among the HSIL 95% were HPV positive, most of which (78%) were single infections with HPV 16 (50%) and HPV 18 (13%). Among tumor samples 99% were HPV positive, most of which (85%) were single infections with HPV16 (63%) and HPV 18 (10%).

Most of the patients (79.6%) were HPV positive. The largest number of HPV positive patients were in the 30-50 years old age category (51.7%), followed by >50 yrs old (24.4%) and <30 yrs old (23.9%). Most of the HPV positive patients were Non-Mapuches (80.1%) and revealed a socio-economic gradient similar to the study population: A Indigent (54%), B Income level ≤US$ 310 (31.8%), and C Income level ≥$451 (14.2%) (Table 3).

EXAMPLE 4

Methylation Profiling with MeDIP-Chip.

Figure 1:
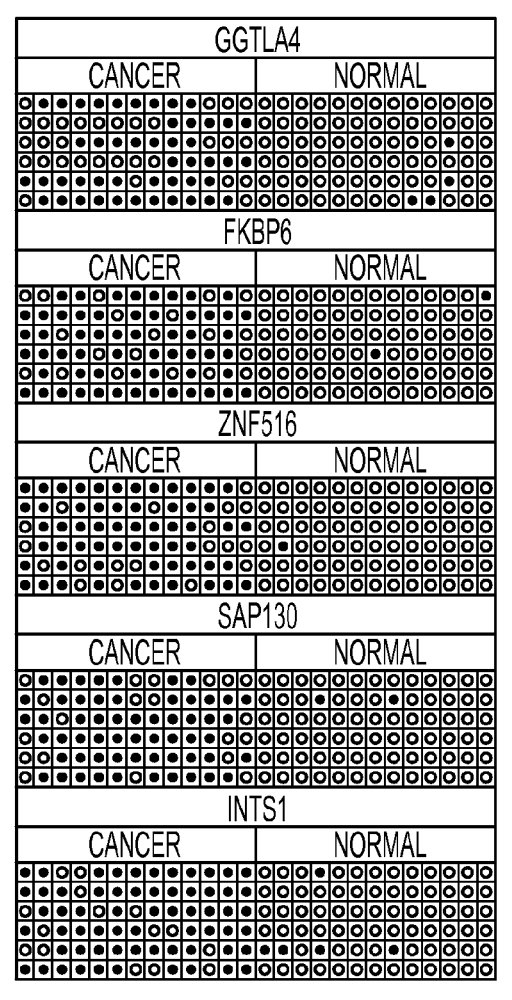

A total of 491 genes were shown to be differentially methylated between normal and cervical cancer samples. Based on the selection criteria, the first 10 genes were selected (GGTLA4, CGB5, FKBP6, TRIM74, ZNF516, MICAL-L2, ZAP701, RGS12, SAP130 and INTS1). These genes were amplified in the same samples used to hybridize microarrays and bisulfite sequencing was performed to examine their methylation status. Amplicons sequence was aligned to the gene of interest using the BLAST algorithms (NCBI) to ascertain their identity. Only five genes were selected as potential biomarkers after bisulfite sequence analysis, GGTLA4, FKBP6, ZNF516, SAP130 and INTS1 (FIG. 1), because these genes had a high percentage of identity (>75%), and were only methylated in cancer samples. Detailed information regarding these five genes can be found in Table 4.

TABLE 3

| | | | | Histology | | | |
|---|---|---|---|---|---|---|---|
| | | n = 221 n (%) | HPV positive n (%) | Normal n (%) | Low Grade n (%) | High Grade n (%) | Carcinoma n (%) |
| Age | <30 yr | 50 (22.6%) | 42 (23.9%) | 6 (24.0%) | 42 (63.6%) | 2 (2.3%) | 0 (0.0%) |
| | 31-50 yr | 121 (54.8%) | 91 (51.7%) | 15 (60.0%) | 22 (33.3%) | 83 (94.3%) | 1 (2.6%) |
| | >50 yr | 50 (22.6%) | 43 (24.4%) | 4 (16.0%) | 2 (3.0%) | 3 (3.4%) | 38 (97.4%) |
| Socioeconomic status | Indigent | 122 (55.2%) | 95 (54.0%) | 15 (60.0%) | 37 (56.1%) | 49 (53.8%) | 21 (53.8%) |
| | ≤US$310/month | 65 (29.4%) | 56 (31.8%) | 5 (20.0%) | 20 (30.3%) | 29 (31.9%) | 11 (28.2%) |
| | >$310/month | 34 (15.4%) | 25 (14.2%) | 5 (20.0%) | 9 (13.6%) | 13 (14.3) | 7 (18.0%) |
| Ethnicity | Non-Mapuche | 172 (77.8%) | 141 (80.1%) | 15 (60.0%) | 55 (83.3%) | 75 (82.4%) | 27 (69.2%) |
| | Mapuche | 49 (22.2%) | 35 (19.9%) | 10 (40.0%) | 11 (16.7%) | 16 (17.6%) | 12 (30.8%) |
| Histology | Normal | 25 (11%) | 1 (4.0%) | — | — | — | — |
| | Low Grade | 66 (29.8%) | 53 (80.3%) | — | — | — | — |
| | High Grade | 91 (41.2%) | 85 (93.4%) | — | — | — | — |
| | Carcinoma | 39 (17.6%) | 37 (94.9) | — | — | — | — |
| HPV status | Negative | 45 (20.3%) | — | 24 (96.0%) | 13 (19.7%) | 6 (6.6%) | 2 (5.1%) |
| | Positive | 176 (79.6%) | — | 1 (4.0%) | 53 (80.3%) | 85 (93.4%) | 37 (94.9) |
| Methylation status | | | | | | | |
| GGTLA | Methylated | 62 (28.5%) | 58 (32.9%) | 1 (4.0%) | 3 (4.5%) | 20 (21.9%) | 38 (97.4%) |
| | Partial Methylation | 71 (32.1%) | 61 (34.7%) | 1 (4.0%) | 22 (33.3%) | 48 (52.7%) | 0 (0.0%) |
| | Unmethylated | 88 (39.8%) | 57 (32.4%) | 23 (92.0%) | 41 (62.1%) | 23 (25.3%) | 1 (2.6%) |
| FKBP6 | Methylated | 114 (51.6%) | 103 (58.5%) | 0 (0.0%) | 40 (60.6%) | 37 (40.7%) | 37 (94.9%) |
| | Partial Methylation | 23 (10.4%) | 19 (10.8%) | 0 (0.0%) | 15 (22.7%) | 7 (7.7%) | 1 (2.6%) |
| | Unmethylated | 84 (38.0%) | 54 (30.7%) | 25 (100.0%) | 11 (16.6%) | 47 (51.6%) | 1 (2.6%) |
| ZNF516 | Methylated | 114 (51.6%) | 43 (24.4%) | 0 (0.0%) | 9 (13.6%) | 5 (5.5%) | 34 (87.2%) |
| | Partial Methylation | 23 (10.4%) | 125 (71.0%) | 0 (0.0%) | 54 (81.8%) | 82 (90.1%) | 5 (12.8%) |
| | Unmethylated | 84 (38.0%) | 8 (4.5%) | 25 (100.0%) | 3 (4.5%) | 4 (4.4%) | 0 (0.0%) |
| INTS1 | Methylated | 38 (17.2%) | 36 (20.5%) | 0 (0.0%) | 3 (4.5%) | 6 (6.6%) | 29 (74.4%) |
| | Partial Methylation | 150 (67.9%) | 131 (74.4%) | 2 (8.0%) | 61 (92.4%) | 78 (85.7%) | 9 (23.1%) |
| | Unmethylated | 33 (14.9%) | 9 (5.1%) | 23 (92.0%) | 2 (3.0%) | 7 (7.7%) | 1 (2.6%) |
| SAP130 | Methylated | 78 (35.3%) | 71 (40.3%) | 0 (0.0%) | 3 (4.5%) | 42 (46.2%) | 33 (84.6%) |
| | Partial Methylation | 58 (26.2%) | 52 (29.5%) | 0 (0.0%) | 23 (34.8%) | 29 (31.9%) | 6 (15.4%) |
| | Unmethylated | 85 (38.5%) | 53 (30.1%) | 25 (100.0%) | 40 (60.6%) | 20 (21.9%) | 0 (0.0%) |

Sociodemographic characteristics, histology, HPV and methylation status of 221 validation samples (Group A)

TABLE 4

Gene symbols, names, and chromosome locations of selected genes

| Symbol | Other names | Chromosome location | Name |
|---|---|---|---|
| GGTLA4 | GGTL6; GGTLA3; GGTLA4; MGC50550; dJ831C21.1; dJ831C21.2; GGTLC1 | 20p11.1 | Gamma-glutamyl transferase-activity 4 |
| FKBP6 | FKBP36; PPIase; MGC87179; FKBP6 | 7q11.23 | FK506, 36 kDa binding proteins |
| ZNF516 | HsT287; ZNF516 | 18q23 | Zinc-finger proteins 516 |
| SAP130 | FLJ12761; SAP130 | 2q14.3 | Associated with the Sin3A, 130 kDa Protein |
| INTS1 | INT1; NET28; FLJ46624; KIAA1440; DKFZp586J0619; INTS1 | 7p22.3 | Integrator complex of subunit 1 |

EXAMPLE 5

Internal Validation of Microarray Results.

Methylation Specific PCR (MSP) was used to examine the methylation profiles of the five genes (GGTLA4, FKBP6, ZNF516, INTS1 and SAP130 in the normal and cervical samples hybridized to the microarrays. The 100% of normal samples showed no methylation, where as the cancer samples were methylated in all cases (100%) (FIG. 2).

External Validation of Microarray Results.

Methylation Specific PCR (MSP) was used to examine the methylation status of GGTLA4, FKBP6, ZNF516, INTS1 and SAP130 in 221 HPV genotyped samples: 25 normal, 66 Low Grade Lesions (LSI), 91 High Grade Lesions (HSIL) and 39 cervical cancers (CC) (FIG. 3).

FIG. 4 shows the frequency of methylation of each gene by histology type. The methylation rates of all five genes (GGTLA4, FKBP6, ZNF516, SAP130 and INTS1) in normal, LSIL, HSIL and SCC were different. In the genes FKBP6, ZNF516, SAP130 and INTS1 there was none in the normal group and only 1 in 25 patients (4.0%) was positive for the GGTLA4 Gene. In the LSIL the frequency of methylation increases for all the genes, GGTLA4 (4.5%), FKBP6 (60.6%), ZNF516 (13.6%), SAP130 (4.5%) and INTS1 (4.5%). In the HSIL the methylation frequency varied. Only the gene GGTLA4, INTS1 and SAP130 increases the rates of methylation (21.9%, 6.6% and 46.2% respectively) and the genes FKBP6 (40.7%) and ZNF516 (5.5%) decreased.

Finally, in the cancer samples, all the genes showed increases of the methylation frequency with frequencies among 74.4% to 97.4% (Table 3). The genes GGTLA4, INTS1 and SAP130 can be seen that the methylation frequency increases with the severity of the cervical lesion. The other genes also showed increases of the methylation frequency, but this decreased in the HSIL. Only the genes GGTLA4, FKBP6 and INTS1, in comparison with the methylation, showed a higher partial methylation in the pre-cancerous lesions. Methylation frequency for all genes was the same across socio-economic status and ethnic groups (results not shown).

EXAMPLE 6

Diagnostic Performance of DNA Methylation Markers.

The sensitivities and specificities of HPV and DNA methylations, alone and in parallel, were determined to assess their usefulness as biomarkers for the diagnosis or screening of patients (Table 5). The sensitivity and specificity for the diagnosis of SCC using HPV testing were 95 and 88%, respectively. SAP130 conferred the best performance with sensitivities of 100% and specificities of 100% for SCC.

TABLE 5

The sensitivities and specificities of HPV testing and DNA methylation for invasive cervical cancer using Methylation Specific PCR.

| | HPV | GGTLA | FKBP6 | ZNF516 | INTS1 | SAP130 |
|---|---|---|---|---|---|---|
| Sensitivity | 94.90% | 97.4% | 97.4% | 97.4% | 97.4% | 100.00% |
| Specificity | 88.00% | 92.0% | 100.0% | 100.0% | 92.0% | 100.00% |

The correlation of cancer status with GGTLA4 methylation (1.00), ZNF516 (0.90), SAP130 (0.90) and FKBP6 (0.87) was higher than with the positive HPV infection (0.80) and INTS1 (0.80) methylation. All correlations were statistically significant at the 95th percentile. All correlations were statistically significant at the 95th percentile. The ROC for HPV and individual genes revealed Area under the Curve values of: HPV (0.95), FKBP6 (0.98), SAP130 (1.00), INTS1 (0.94), GGTLA4 (0.94) and ZNF516 (1.00).

EXAMPLE 7

Ingenuity Pathways Analysis (IPA).

Figure 5A:
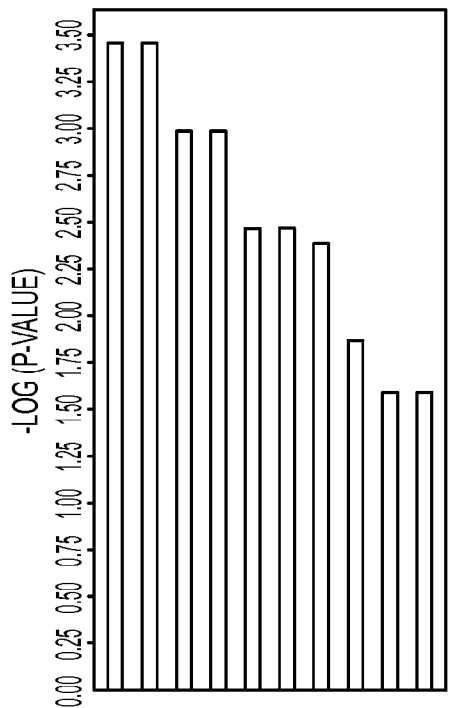
FIG. 5A-5B. Ingenuity pathway analyses.
Figure 5B:
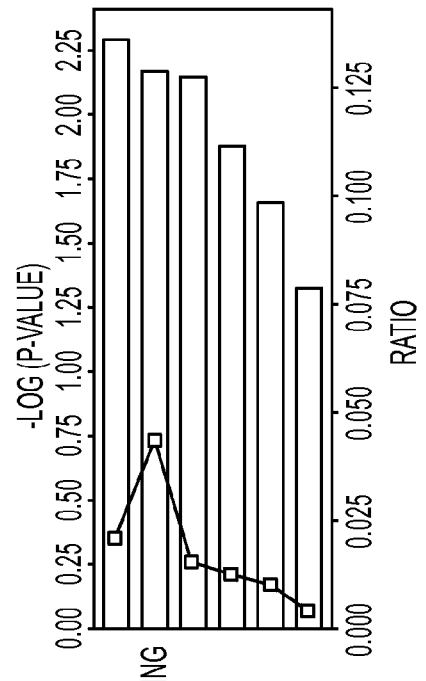
Figure 6A:
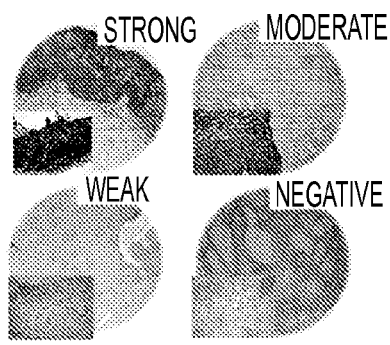
FIGS. 6A-6D. Representative images of antibody staining for strong, moderate, weak and negative signals.
Figure 6B:
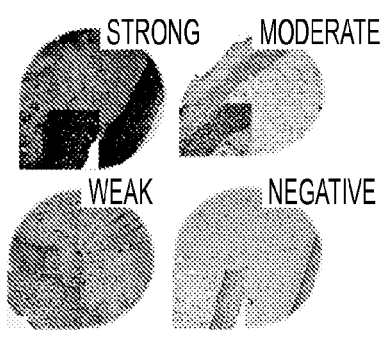
Figure 6C:
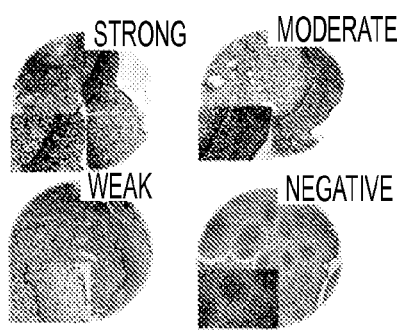
Figure 6D:
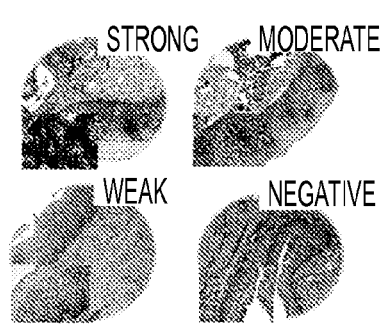
Figure 7A:
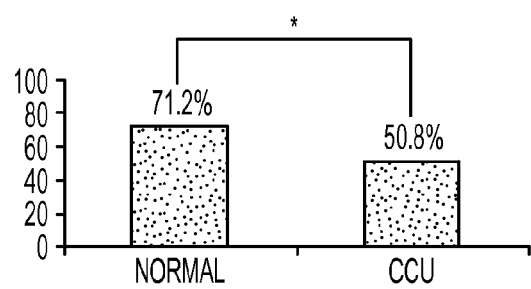
FIGS. 7A-7D. Frequency of positive immunohistochemistry staining expression in normal cervical mucosa and cervical carcinoma tissues.
Figure 7B:
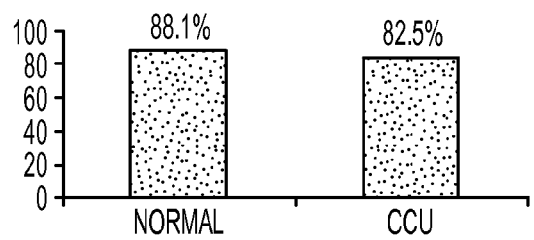
Figure 7C:
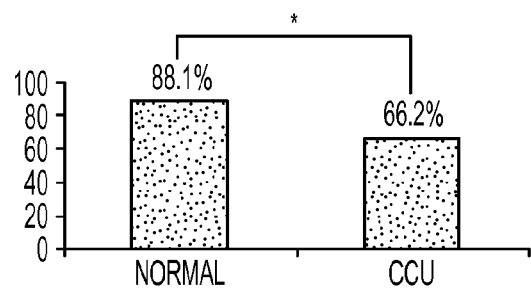
Figure 7D:
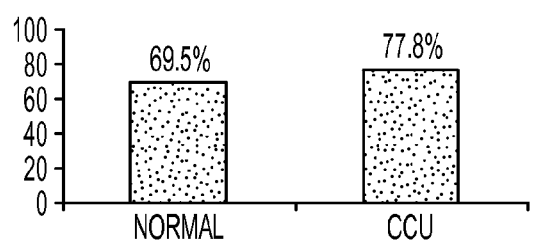

Gene networks and canonical pathways representing key genes were identified using the curated Ingenuity Pathways Analysis (IPA) database as previously described [26]. Ingenuity Pathway Analysis further categorized our data set into functional categories and networks. The Gene ontology analyses of these candidate hypermethylated genes revealed a broad representation of all the common functions of cancer cells, such as Cellular Growth and Proliferation, Cell Cycle, Gene Expression among others. Also, the genes are involved in the pathways of DNA Methylation and Transcriptional Repression Signaling (FIG. 5). This latter observation is of particular interest because the genes we have identified are hypermethylated in the promoter region and/or CpG islands of genes that may be transcriptionally repressed in cervical cancer cells or in precursor lesions.

Association of DNA Methylation and Immunohistochemical Expression.

Immunohistochemistry (IHQ) was performed to identify expression of genes at protein level in a separate cohort of 122 samples. The proteins of GGTLA4, FKBP6, and ZNF516 were detected in the cytoplasm and nucleus, but INTS1 was detected only in the cytoplasm (FIG. 6).

The socio-demographic characteristics, histology, HPV infection status, and immunohistochemical expression are listed in Table 6. The majority of patients are indigent non-Mapuche women over 50 yrs old, with similar distribution of histology and HPV status.

TABLE 6

Sociodemographic characteristics, histology, HPV infection and, immunohistochemical expression of 122 validation samples (Group B).

| | | n = 122 n (%) | Normal Histology n (%) | Carcinoma Histology n (%) |
|---|---|---|---|---|
| Age | <30 yr | 13 (10.7%) | 13 (22.0%) | 0 (0.0%) |
| | 31-50 yr | 48 (39.3%) | 24 (40.7%) | 24 (38.1%) |
| | >50 yr | 61 (50.0%) | 22 (37.3%) | 39 (61.9%) |
| Socioeconomic status | Indigent | 57 (46.7%) | 29 (49.15%) | 28 (44.44%) |
| | ≤US $310/month | 48 (39.3%) | 22 (37.29%) | 26 (41.27%) |
| | >$310/month | 17 (13.9%) | 8 (13.56%) | 9 (14.29%) |
| Ethnicity | Non-Mapuche | 87 (71.3%) | 17 (28.81%) | 18 (28.57%) |
| | Mapuche | 35 (28.7%) | 42 (71.19%) | 45 (71.43%) |
| Histology | Normal | 59 (48.4%) | — | — |
| | Carcinoma | 63 (51.6%) | — | — |
| HPV status | Negative | 57 (46.7%) | 53 (89.8%) | 4 (6.3%) |
| | Positive | 65 (53.3%) | 6 (10.2%) | 59 (93.7%) |
| Immunohistochemical expression | | | | |
| GGTLA | Positive | 74 (60.7%) | 42 (71.2%) | 32 (50.8%)* |
| | Negative | 48 (39.3%) | 17 (28.8%) | 31 (49.2%) |
| FKBP6 | Positive | 104 (85.2%) | 52 (88.1%) | 52 (82.5%) |
| | Negative | 18 (14.8%) | 7 (11.9%) | 11 (17.5%) |
| ZNF516 | Positive | 100 (82.0%) | 52 (88.1%) | 48 (76.2%)* |
| | Negative | 22 (18.0%) | 7 (11.9%) | 15 (23.8%) |
| INTS1 | Positive | 89 (73.0%) | 41 (69.5%) | 49 (77.8%) |
| | Negative | 33 (27.0%) | 18 (30.5%) | 14 (22.2%) |

*t-test p-value <0.05

GGTLA4 (50.8%) and ZNF516 (66.2%) showed a statistically significant reduction of the immunohistochemical expression in tumor when compared to normal cervical epithelium: GGTLA4 (71.2%) and ZNF516 (88.1%) (p-value <0.05).

References

The disclosure of each reference cited is expressly incorporated herein.

1. Dehn, D., K. C. Torkko, and K. R. Shroyer, *Human papillomavirus testing and molecular markers of cervical dysplasia and carcinoma*. Cancer 2007. 111(1): p. 1-14.
2. Beaudenon, S. and J. M. Huibregtse, *HPV E6, E6AP and cervical cancer*. BMC Biochem, 2008. 9 Suppl 1: p. S4.
3. Solomon, D., M. Schiffman, and R. Tarone, *Comparison of three management strategies for patients with atypical squamous cells of undetermined significance: baseline results from a randomized trial*. J Natl Cancer Inst, 2001. 93(4): p. 293-9.
4. Schorge, J. O., et al., *P16 as a molecular biomarker of cervical adenocarcinoma*. Am J Obstet Gynecol, 2004. 190(3): p. 668-73.
5. Tringler, B., et al., *Evaluation of p16INK4a and pRb expression in cervical squamous and glandular neoplasia*. Hum Pathol, 2004. 35(6): p. 689-96.
6. Trunk, M. J., et al., *Morphologic characteristics of p16INK4a-positive cells in cervical cytology samples*. Acta Cytol, 2004. 48(6): p. 771-82.
7. Narisawa-Saito, M. and T. Kiyono, *Basic mechanisms of high-risk human papillomavirus-induced carcinogenesis: roles of E6 and E7 proteins*. Cancer Sci, 2007. 98(10): p. 1505-11.
8. Clifford, G. M., et al., *Comparison of HPV type distribution in high-grade cervical lesions and cervical cancer: a meta-analysis*. Br J Cancer, 2003. 89(1): p. 101-5.
9. Clifford, G. M., et al., *Worldwide distribution of human papillomavirus types in cytologically normal women in the International Agency for Research on Cancer HPV prevalence surveys: a pooled analysis*. Lancet, 2005. 366(9490): p. 991-8.
10. Clifford, G. M., et al., *Human papillomavirus genotype distribution in low-grade cervical lesions: comparison by geographic region and with cervical cancer*. Cancer Epidemiol Biomarkers Prev, 2005. 14(5): p. 1157-64.
11. Clifford, G. M., et al., *Human papillomavirus types in invasive cervical cancer worldwide: a meta-analysis*. Br J Cancer, 2003. 88(1): p. 63-73.
12. Burd, E. M., *Human papillomavirus and cervical cancer*. Clin Microbiol Rev, 2003. 16(1): p. 1-17.
13. Minaguchi, T. and H. Yoshikawa, [*Molecular mechanism of cervical carcinogenesis*]. Gan To Kagaku Ryoho, 2010. 37(1): p. 18-22.
14. Wentzensen, N., et al., *Utility of methylation markers in cervical cancer early detection: appraisal of the state-of-the-science*. Gynecol Oncol, 2009. 112(2): p. 293-9.
15. Mayrand, M. H., et al., *Human papillomavirus DNA versus Papanicolaou screening tests for cervical cancer*. N Engl J Med, 2007. 357(16): p. 1579-88.
16. Shivapurkar, N., et al., *Evaluation of candidate methylation markers to detect cervical neoplasia*. Gynecol Oncol, 2007. 107(3): p. 549-53.
17. Esteller, M., *Epigenetics in cancer*. N Engl J Med, 2008. 358(11): p. 1148-59.
18. Giacinti, L., P. Vici, and M. Lopez, *Epigenome: a new target in cancer therapy*. Clin Ter, 2008. 159(5): p. 347-60.
19. Vucic, E. A., et al., *Methylation analysis by DNA immunoprecipitation (MeDIP)*. Methods Mol Biol, 2009. 556: p. 141-53.
20. Apostolidou, S., et al., *DNA methylation analysis in liquid-based cytology for cervical cancer screening*. Int J Cancer, 2009. 125(12): p. 2995-3002.
21. Hogue, M. O., et al., *Genome-wide genetic characterization of bladder cancer: a comparison of high-density single-nucleotide polymorphism arrays and PCR-based microsatellite analysis*. Cancer Res, 2003. 63(9): p. 2216-22.
22. van den Brule, A. J., et al., *GP5+/6+ PCR followed by reverse line blot analysis enables rapid and high-throughput identification of human papillomavirus genotypes. J Clin Microbiol, 2002. 40(3): p. 779-87.
23. Scacheri, P. C., G. E. Crawford, and S. Davis, *Statistics for ChIP-chip and DNase hypersensitivity experiments on NimbleGen arrays*. Methods Enzymol, 2006. 411: p. 270-82.
24. Herman, J. G., et al., *Methylation-specific PCR: a novel PCR assay for methylation status of CpG islands*. Proc Natl Acad Sci USA, 1996. 93(18): p. 9821-6.
25. Sun, X. W., et al., *Human papillomavirus infection in women infected with the human immunodeficiency virus*. N Engl J Med, 1997. 337(19): p. 1343-9.
26. Rodenhiser, D. I., et al., *Epigenetic mapping and functional analysis in a breast cancer metastasis model using whole-genome promoter tiling microarrays*. Breast Cancer Res, 2008. 10(4): p. R62.
27. Mulero-Navarro, S. and M. Esteller, *Epigenetic biomarkers for human cancer: The time is now*. Crit Rev Oncol Hematol, 2008.
28. website at ncbi host, nlm domain, nih.gov directory, guide file
29. Fleischer, T. C., U. J. Yun, and D. E. Ayer, *Identification and characterization of three new components of the mSin3A corepressor complex*. Mol Cell Biol, 2003. 23(10): p. 3456-67.
30. Baillat, D., et al., *Integrator, a multiprotein mediator of small nuclear RNA processing, associates with the C-terminal repeat of RNA polymerase II*. Cell, 2005. 123(2): p. 265-76.
31. Gebhard, C., et al., *Genome-wide profiling of CpG methylation identifies novel targets of aberrant hypermethylation in myeloid leukemia*. Cancer Res, 2006. 66(12): p. 6118-28.
32. Jacinto, F. V., et al., *Discovery of epigenetically silenced genes by methylated DNA immunoprecipitation in colon cancer cells*. Cancer Res, 2007. 67(24): p. 11481-6.
33. Jacinto, F. V., E. Ballestar, and M. Esteller, *Methyl-DNA immunoprecipitation (MeDIP): hunting down the DNA methylome*. Biotechniques, 2008. 44(1): p. 35, 37, 39 passim.
34. Jin, S. G., S. Kadam, and G. P. Pfeifer, *Examination of the specificity of DNA methylation profiling techniques towards 5-methylcytosine and 5-hydroxymethylcytosine*. Nucleic Acids Res, 2010. 38(11): p. e125.
35. Movassagh, M., et al., *Differential DNA methylation correlates with differential expression of angiogenic factors in human heart failure*. PLoS One, 2010. 5(1): p. e8564.
36. Weber, M., et al., *Chromosome-wide and promoter-specific analyses identify sites of differential DNA methylation in normal and transformed human cells*. Nat Genet, 2005. 37(8): p. 853-62.
37. Kron, K., et al., *Discovery of novel hypermethylated genes in prostate cancer using genomic CpG island microarrays*. PLoS One, 2009. 4(3): p. e4830.
38. Weng, Y. I., T. H. Huang, and P. S. Yan, *Methylated DNA immunoprecipitation and microarray-based analysis: detection of DNA methylation in breast cancer cell lines*. Methods Mol Biol, 2009. 590: p. 165-76.
39. Lai, H. C., et al., *Identification of novel DNA methylation markers in cervical cancer*. Int J Cancer, 2008. 123(1): p. 161-7.
40. Yamashita, K., et al., *Pharmacologic unmasking of epigenetically silenced tumor suppressor genes in esophageal squamous cell carcinoma*. Cancer Cell, 2002. 2(6): p. 485-95.
41. Knudson, A. G., Jr., *Mutation and cancer: statistical study of retinoblastoma*. Proc Natl Acad Sci USA, 1971. 68(4): p. 820-3.
42. Jones, P. A. and P. W. Laird, *Cancer epigenetics comes of age*. Nat Genet, 1999. 21(2): p. 163-7.
43. Herman, J. G. and S. B. Baylin, *Gene silencing in cancer in association with promoter hypermethylation*. N Engl J Med, 2003. 349(21): p. 2042-54.
44. Espada, J. and M. Esteller, *DNA methylation and the functional organization of the nuclear compartment*. Semin Cell Dev Biol, 2010. 21(2): p. 238-46.
45. Kass, S. U., D. Pruss, and A. P. Wolffe, *How does DNA methylation repress transcription?* Trends Genet, 1997. 13(11): p. 444-9.
46. Hogue, M. O., et al., *Genome-wide promoter analysis uncovers portions of the cancer methylome*. Cancer Res, 2008. 68(8): p. 2661-70.
47. Yamashita, K., et al., *HOP/OB1/NECC1 promoter DNA is frequently hypermethylated and involved in tumorigenic ability in esophageal squamous cell carcinoma*. Mol Cancer Res, 2008. 6(1): p. 31-41.
48. Runowicz, C. D., *Molecular screening for cervical cancer—time to give up Pap tests?* N Engl J Med, 2007. 357(16): p. 1650-3.
49. Ault, K. A., *Epidemiology and natural history of human papillomavirus infections in the female genital tract*. Infect Dis Obstet Gynecol, 2006. 2006 Suppl: p. 40470.
50. Chan, J. K. and J. S. Berek, *Impact of the human papilloma vaccine on cervical cancer*. J Clin Oncol, 2007. 25(20): p. 2975-82.
51. Pollack, A. E., et al., *Ensuring access to HPV vaccines through integrated services: a reproductive health perspective*. Bull World Health Organ, 2007. 85(1): p. 57-63.
52. Boot, H. J., et al., *Assessing the introduction of universal human papillomavirus vaccination for preadolescent girls in The Netherlands*. Vaccine, 2007. 25(33): p. 6245-56.
53. Lowy, D. R. and J. T. Schiller, *Prophylactic human papillomavirus vaccines*. J Clin Invest, 2006. 116(5): p. 1167-73.
54. Mandavi, A. and B. J. Monk, *Vaccines against human papillomavirus and cervical cancer: promises and challenges*. Oncologist, 2005. 10(7): p. 528-38.
55. Lie, A. K. and G. Kristensen, *Human papillomavirus E6/E7 mRNA testing as a predictive marker for cervical carcinoma*. Expert Rev Mol Diagn, 2008. 8(4): p. 405-15.
56. Boulet, G. A., et al., *Human papillomavirus in cervical cancer screening: important role as biomarker*. Cancer Epidemiol Biomarkers Prev, 2008. 17(4): p. 810-7.
57. Murphy, N., et al., *p16INK4A, CDC6, and MCM5: predictive biomarkers in cervical preinvasive neoplasia and cervical cancer*. J Clin Pathol, 2005. 58(5): p. 525-34.
58. Melsheimer, P., et al., *DNA aneuploidy and integration of human papillomavirus type 16 e6/e7 oncogenes in intraepithelial neoplasia and invasive squamous cell carcinoma of the cervix uteri*. Clin Cancer Res, 2004. 10(9): p. 3059-63.
59. Wentzensen, N., S. Vinokurova, and M. von Knebel Doeberitz, *Systematic review of genomic integration sites of human papillomavirus genomes in epithelial dysplasia and invasive cancer of the female lower genital tract*. Cancer Res, 2004. 64(11): p. 3878-84.
60. Kruse, A. J., et al., *Evaluation of MIB-1-positive cell clusters as a diagnostic marker for cervical intraepithelial neoplasia*. Am J Surg Pathol, 2002. 26(11): p. 1501-7.
61. Spitzer, M., B. S. Apgar, and G. L. Brotzman, *Management of histologic abnormalities of the cervix*. Am Fam Physician, 2006. 73(1): p. 105-12.

62. Ault, K. A., et al., *Telomerase activity as a potential diagnostic marker for triage of abnormal Pap smears.* J Low Genit Tract Dis, 2005. 9(2): p. 93-9.
63. Yang, J. K., *FLIP as an anti-cancer therapeutic target.* Yonsei Med J, 2008. 49(1): p. 19-27.
64. Nees, M., et al., *Identification of novel molecular markers which correlate with HPV-induced tumor progression.* Oncogene, 1998. 16(19): p. 2447-58.
65. Unger, E. R., et al., *Molecular markers for early detection of cervical neoplasia.* Dis Markers, 2004. 20(2): p. 103-16.

We claim:

1. A method for identifying cervical cancer in a human, comprising:
    a) obtaining nucleic acid from a test sample from the human;
    b) performing bisulfite modification to the nucleic acid in a);
    c) performing quantitative real-time methylation specific PCR (QMSP) on bisulfite modified nucleic acid from b) using PCR primers and probes specific for a promoter region of one or more genes of interest, wherein the one or more genes of interest are selected from the group consisting of GGTLA4, FKBP6, ZNF516, SAP130, and INTS1, and the primers and probes are selected from the group consisting of SEQ ID NOS: 23-42;
    d) determining a promoter methylation level of the promoter regions of the one or more genes of interest in the nucleic acid from the test sample of the human;
    e) providing a reference non-neoplastic test sample;
    f) comparing the level of promoter methylation of the one or more genes of interest from the test sample of the human, to the level of promoter methylation of the one or more genes of interest in a reference non-neoplastic test sample; and
    g) identifying said human as having cervical cancer when the level of promoter methylation of the one or more genes of interest in the test sample of the human, is increased relative to the level of promoter methylation of the one or more genes of interest in a reference non-neoplastic test sample indicating epigenetic silencing of the one or more genes of interest.

2. The method of claim 1 wherein the test sample from the human of step a) is from a specimen selected from the group consisting of a tissue specimen, a biopsy specimen, a surgical specimen, a cervical swab, and a cytological specimen.

3. The method of claim 1 wherein epigenetic silencing of at least two of said genes is detected.

4. The method of claim 1 wherein epigenetic silencing of at least three of said genes is detected.

5. The method of claim 1 wherein epigenetic silencing of at least four of said genes is detected.

6. The method of claim 1 wherein epigenetic silencing of five of said genes is detected.

7. The method of claim 1 wherein epigenetic silencing of at least GGTLA4 and ZNF516 is determined.

* * * * *

UNITED STATES PATENT AND TRADEMARK OFFICE
CERTIFICATE OF CORRECTION

PATENT NO. : 8,859,468 B2
APPLICATION NO. : 13/634318
DATED : October 14, 2014
INVENTOR(S) : Rafael Enrique Guerrero-Preston, David Sidransky and Priscilla Brebi-Mieville It is certified that error appears in the above-identified patent and that said Letters Patent is hereby corrected as shown below:

In the claims:

Column 39, lines 42-49, Claim 1. c) should read -- c) performing methylation specific PCR (MSP) on bisulfite modified nucleic acid from b) using PCR primers specific for a promoter region of one or more genes of interest, wherein the one or more genes of interest are selected from the group consisting of GGTLA4, FKBP6, ZNF516, SAP130, and INTS1, and the primers are selected from the group consisting of SEQ ID NOS: 23-42;

Signed and Sealed this
Twenty-eighth Day of June, 2016

Michelle K. Lee
*Director of the United States Patent and Trademark Office*